US012655265B2

(12) United States Patent
Dorman et al.

(10) Patent No.: US 12,655,265 B2
(45) Date of Patent: Jun. 16, 2026

(54) LOW-TEMPERATURE PLASTIC DEPOLYMERIZATION

(71) Applicant: Board of Supervisors of Louisiana State University and Agricultural and Mechanical College, Baton Rouge, LA (US)

(72) Inventors: James Anthony Dorman, Baton Rouge, LA (US); Kerry Dooley, Baton Rouge, LA (US); Bernard Whajah, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 268 days.

(21) Appl. No.: 18/699,338

(22) PCT Filed: Oct. 11, 2022

(86) PCT No.: PCT/US2022/077871
§ 371 (c)(1),
(2) Date: Apr. 8, 2024

(87) PCT Pub. No.: WO2023/064741
PCT Pub. Date: Apr. 20, 2023

(65) Prior Publication Data
US 2025/0236715 A1 Jul. 24, 2025

Related U.S. Application Data

(60) Provisional application No. 63/255,048, filed on Oct. 13, 2021.

(51) Int. Cl.
*C08J 11/16* (2006.01)
*B01J 21/06* (2006.01)
(Continued)

(52) U.S. Cl.
CPC ............ *C08J 11/16* (2013.01); *B01J 21/066* (2013.01); *B01J 23/10* (2013.01); *B01J 23/745* (2013.01);
(Continued)

(58) Field of Classification Search
CPC . Y02W 30/62; C08F 8/50; C07C 4/22; C10G 1/10; C08J 11/16; C08J 11/12;
(Continued)

(56) References Cited

U.S. PATENT DOCUMENTS 5,837,088 A 11/1998 Palmgren et al.
6,184,427 B1 2/2001 Klepfer et al.
(Continued)

FOREIGN PATENT DOCUMENTS

CN 111420698 A 7/2017
CN 111604086 A 9/2020
WO WO2020/036532 A1 2/2020

*Primary Examiner* — Vishal V Vasisth
(74) *Attorney, Agent, or Firm* — Thomas | Horstemeyer, LLP

(57) ABSTRACT

In one aspect, the disclosure relates to a method for depolymerizing plastics using radio frequency (RF) induction heating. The method can be conducted at low temperatures and does not require the addition of $H_2$ or solvents. In one aspect, the method is tunable to produce commercially valuable $C_2$-$C_{20}$ compounds including, but not limited to, alkenes, cycloalkanes, cycloalkenes, hydrocarbon lubricants, and polymerizable monomers. In another aspect, the method can depolymerize both virgin plastics and recycled plastic materials. In still another aspect, catalysts useful in the disclosed method are resistant to coking and poisoning.

19 Claims, 21 Drawing Sheets

(51) Int. Cl.

| | |
|---|---|
| *B01J 23/10* | (2006.01) |
| *B01J 23/745* | (2006.01) |
| *B01J 23/755* | (2006.01) |
| *B01J 29/035* | (2006.01) |
| *B01J 29/44* | (2006.01) |
| *B01J 29/46* | (2006.01) |
| *B01J 29/62* | (2006.01) |
| *B01J 29/68* | (2006.01) |
| *B01J 29/74* | (2006.01) |
| *B01J 29/76* | (2006.01) |
| *B01J 35/33* | (2024.01) |
| *C07C 4/22* | (2006.01) |

(52) U.S. Cl.
CPC ......... *B01J 23/755* (2013.01); *B01J 29/0356* (2013.01); *B01J 29/44* (2013.01); *B01J 29/46* (2013.01); *B01J 29/62* (2013.01); *B01J 29/68* (2013.01); *B01J 29/743* (2013.01); *B01J* *29/7484* (2013.01); *B01J 29/7615* (2013.01); *B01J 35/33* (2024.01); *C07C 4/22* (2013.01); *C08J 2323/06* (2013.01)

(58) Field of Classification Search
CPC ...... C08J 2323/06; B01J 29/44; B01J 23/755; B01J 29/46; B01J 29/743; B01J 23/745; B01J 21/066; B01J 23/10; B01J 29/0333; B01J 29/0359; B01J 29/68; B01J 29/7615; B01J 29/7484; B01J 35/33; B01J 23/83; B01J 29/62
See application file for complete search history.

(56) References Cited

U.S. PATENT DOCUMENTS

| | | | |
|---|---|---|---|
| 8,466,332 | B1 | 6/2013 | Hemmings et al. |
| 2014/0134533 | A1 | 5/2014 | Sacripante et al. |
| 2017/0019116 | A1 | 1/2017 | Chen et al. |

LOW-TEMPERATURE PLASTIC DEPOLYMERIZATION

CROSS REFERENCE TO RELATED APPLICATIONS

This application is a U.S. national phase application under 35 U.S.C. 371 of International Patent Application No. PCT/US2022/077871, filed on Oct. 11, 2022, which claims the benefit of and priority to U.S. Provisional Application No. 63/255,048 filed on Oct. 13, 2021 both of which are incorporated herein by reference in their entireties.

STATEMENT REGARDING FEDERALLY SPONSORED RESEARCH OR DEVELOPMENT

This invention was made with government support under grant number CBET-1805785, awarded by the National Science Foundation. The government has certain rights in the invention.

BACKGROUND

The production of polymers consumes about 5% of the world's gas and oil, mostly as feedstocks and fuels for polymerization processes, with global production at 400 mmt in 2015, rising at >4%/yr, and 95% of this production from synthetics. Despite the substantial amounts of polymers potentially available for reutilization, it has been estimated that of all synthetic polymers produced since 1950, only 7% have been recycled, compared to 60% which have been discarded (lifetimes>20 yr), with the rest of these materials either still in use or incinerated. Polyolefins such as low- and high-density polyethylene (LDPE/HDPE) are among the materials with the lowest rate of decomposition in the environment. Current approaches to recycling plastics have many constraints, making these processes insufficient to curtail the increasing amounts of plastic waste. For example, plastics pyrolysis is limited by economic considerations—it requires high operating temperatures and results in an unwieldy product distribution with little value other than as low-grade fuel.

Numerous start-up companies thermally convert plastics into mixed synthetic light sweet crude. The yields for these technologies range between 40-80%, generally producing higher molecular weight products (kerosenes and oils). While little is known about the commercial processes, there have been recent reports discussing the hydrogenolysis of PE over $Zr/SiO_2$—$Al_2O_3$ and $Ru/CeO_2$. These reactions require high $H_2$ pressures (60 bar) to generate a range of $C_2$-$C_{10}$ hydrocarbons, with products dependent on temperature, $H_2$ pressure, and catalytic metal size/type. To generate lubricant grade materials, Celik et. al used Pt-decorated $SrTiO_3$ (STO) resulting in an average product of ~$C_{30}$ hydrocarbons (280° C., 11.7 bar $H_2$). However, production of lower-molecular weight materials (for example, <$C_{20}$ hydrocarbons), especially in the absence of high $H_2$ pressure, remains unexplored.

More acidic supports such as zeolites can also depolymerize polyolefins. While in some cases (Pt-BEA) high $H_2$ pressures are required, others have shown that low-pressure reactions can occur over H-ZSM-5 or H-Y zeolites. The process requires higher temperatures (>400° C.), with generally low selectivities depending on polymer composition and zeolite structure. Highly selective reactions requiring lower temperatures have yet to be achieved.

Microwave or radiofrequency (RF) induction heating have been explored as alternatives to thermal heating since the electromagnetic radiation can directly interact with the polymer and catalyst. Microwave heating has the advantage that the frequency is tunable to selectively target specific bonds. Unfortunately, microwave-assisted depolymerization processes require the use of solvents to prevent runaway catalyst heating and localized pyrolysis, which results in a carbon product along with the light gases.

Other depolymerization processes require solvents and/or expensive reactors, or may involve catalysts susceptible to coking and/or poisoning from contaminants (e.g. food residue) or plastics processing additives (e.g. flame retardants, plasticizers, and the like).

Despite advances in plastics depolymerization research, there is still a scarcity of methods for depolymerizing plastics that can proceed at low temperatures in the absence of $H_2$ and/or solvents, that offer product selectivity including desirable lower molecular weight $C_2$-$C_{20}$ compounds such as alkenes, cycloalkanes, cycloalkenes, hydrocarbon lubricants and polymerizable monomers in high yields, and that work on both virgin and recycled plastic materials. An ideal method would be economical and would make use of a catalyst resistant to coking and poisoning. These needs and other needs are satisfied by the present disclosure.

SUMMARY

In accordance with the purpose(s) of the present disclosure, as embodied and broadly described herein, the disclosure, in one aspect, relates to a method for depolymerizing plastics using radio frequency (RF) induction heating. The method can be conducted at low temperatures and does not require the addition of $H_2$ or solvents. In one aspect, the method is tunable to produce commercially valuable $C_2$-$C_{20}$ compounds including, but not limited to, alkenes, cycloalkanes, cycloalkenes, hydrocarbon lubricants, and polymerizable monomers. In another aspect, the method can depolymerize both virgin plastics and recycled plastic materials. In still another aspect, catalysts useful in the disclosed method are resistant to coking and poisoning.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figure 2:
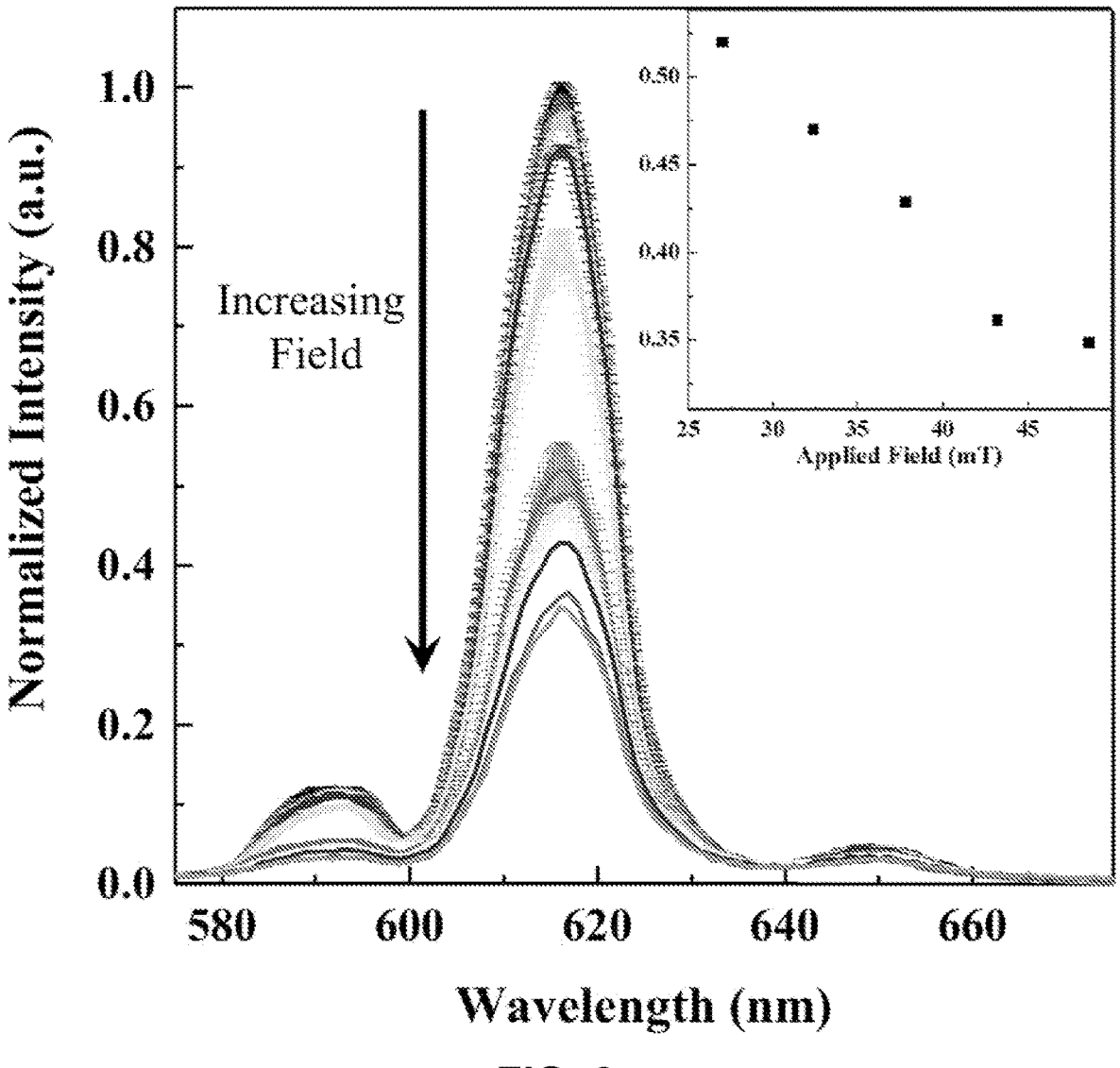

FIG. 2 shows PL response of $Fe_3O_4$/$YVO_4$:$Eu^{3+}$ mixture under applied RF fields. The inset highlights the linear response of the normalized intensity at high applied fields (200-400° C.).

Figure 3:
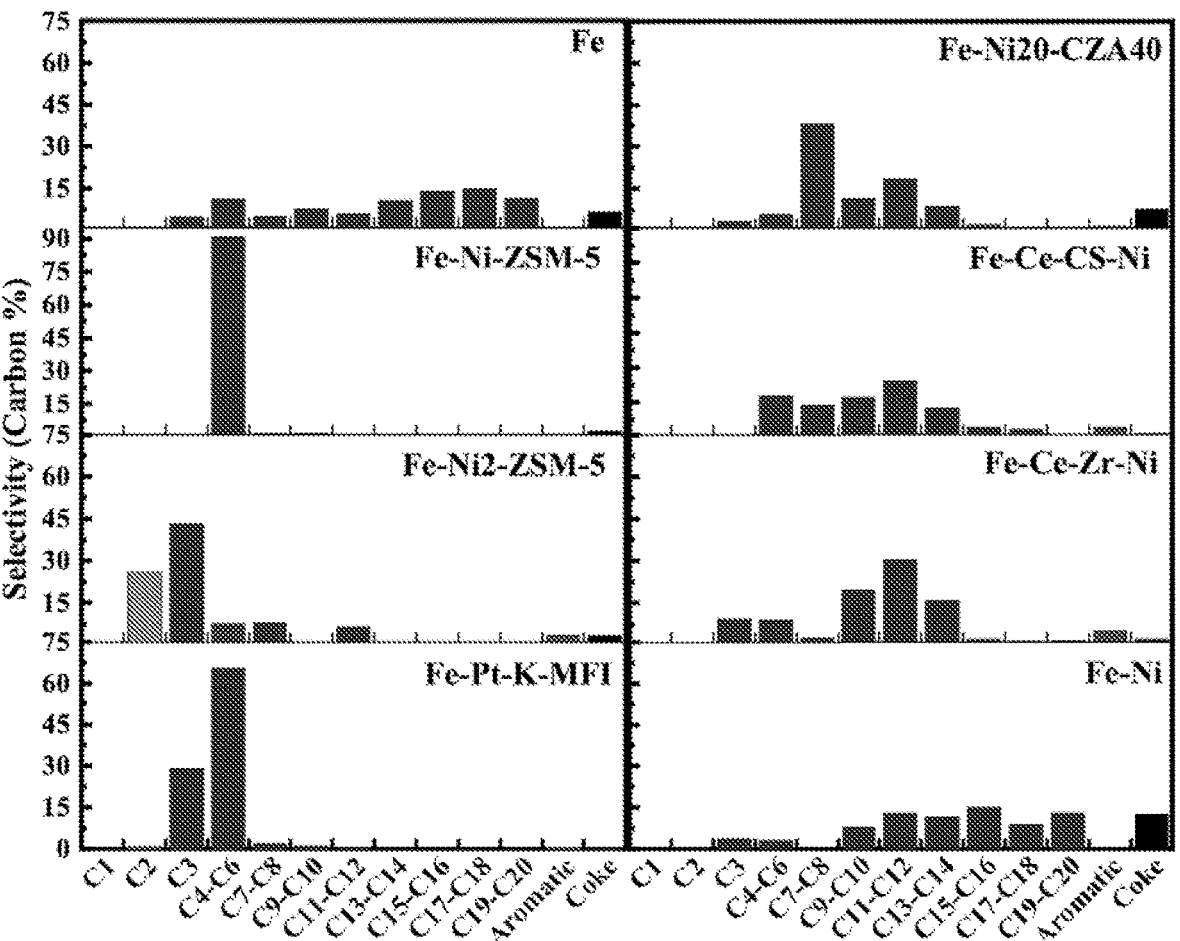

FIG. 3 shows RF (64 mT field)-initiated LDPE depolymerization for various zeolite (left) and non-zeolite (right) catalysts. The different colors are just an aid to the eye. The "Fe" in all but Fe—Ni denotes that 50 wt % of the catalyst is $Fe_3O_4$ nanoparticles. For Fe—Ni, there are 97.6 wt % $Fe_3O_4$ nanoparticles, 115 mg total catalyst.

FIGS. 4A-4D show coke and acid sites analysis. TPO weight derivatives for used, extracted catalysts after LDPE depolymerization for (FIG. 4A) Catalysts containing $CeO_2$, (FIG. 4B) $Fe_3O_4$ and Ni-supported on $Fe_3O_4$, and the (FIG. 4C) zeolite catalysts. The presence of coke is seen from the peaks at above 420° C. (FIG. 4D) Differential thermal analysis of amine desorption of the three ZSM-5-based catalysts. Peaks A and B arise from desorption of weakly adsorbed 1-PA not on Brønsted sites, peak C from the Hofmann elimination of 1-PA to propene and $NH_3$ on Brønsted sites, and D from dehydrogenation chemistry on strong Lewis sites, normally associated with extra-framework $Al^{3+}$. The Si/Al molar ratio obtained by MAS-NMR for H-ZSM-5 is 20, while the ratio computed from these data is 21. The small "C" peak for Ni-ZSM-5 corresponds to <10% residual $H^+$.

Figure 5:
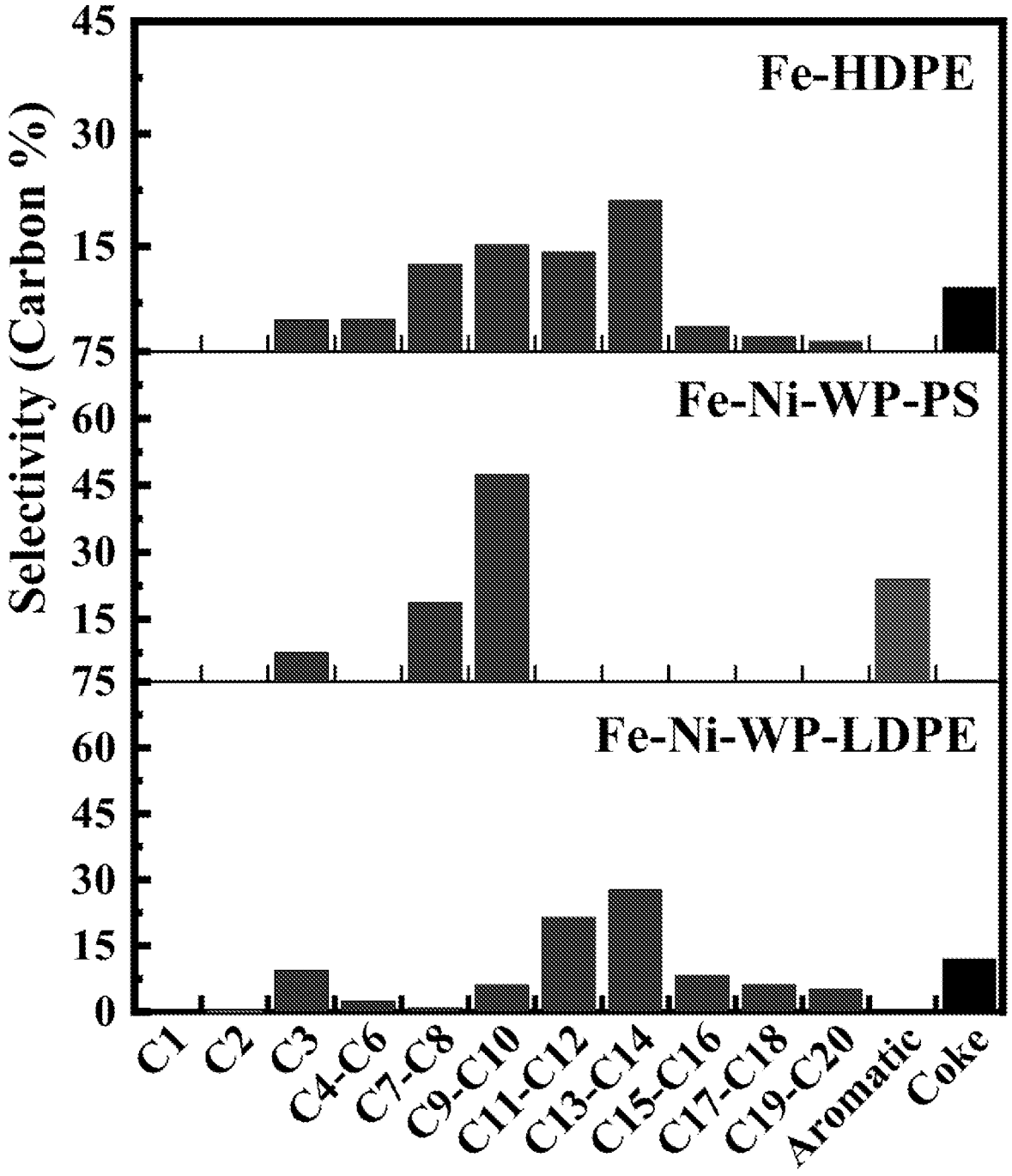

FIG. 5 shows RF-initiated commercial LDPE reaction. Product distribution of commercial LDPE(WP-LDPE) and polystyrene (WP-PS) over Fe—Ni catalysts and virgin HDPE over the Fe catalyst exposed to 64 mT RF field for 2 h.

Figure 6:
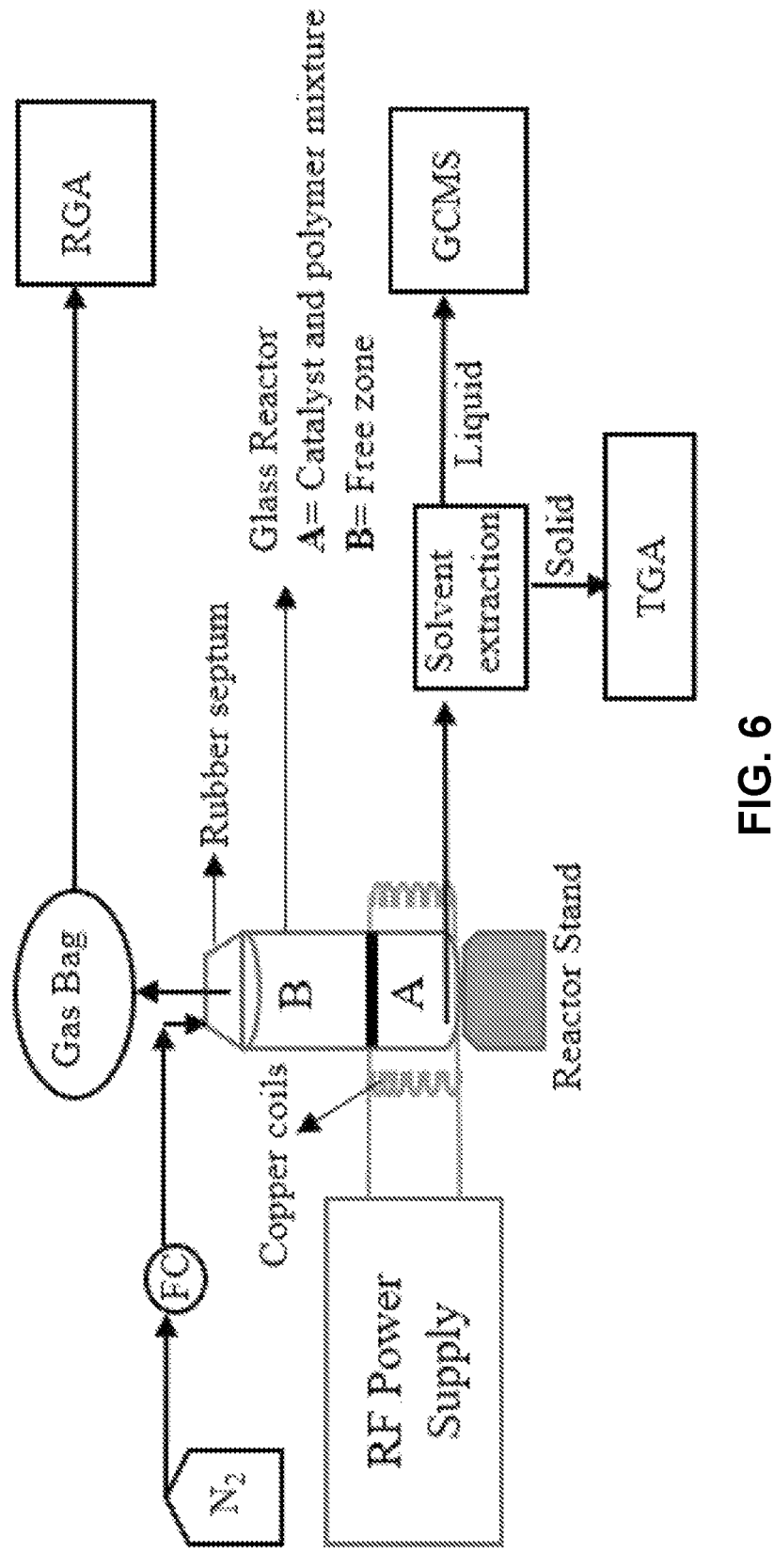

FIG. 6 shows a schematic of a disclosed reactor system and product characterization.

Figure 7A:
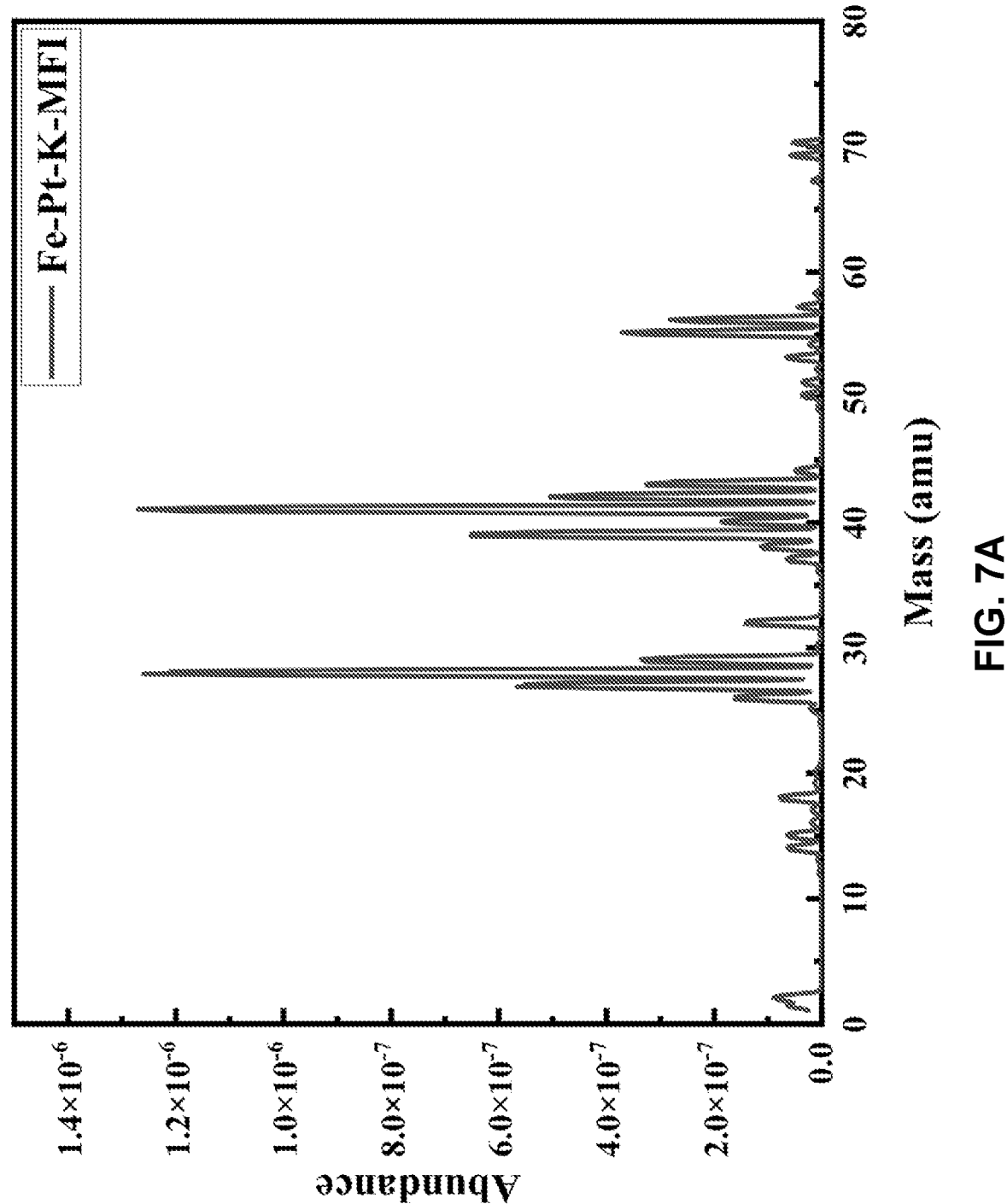
Figure 7B:
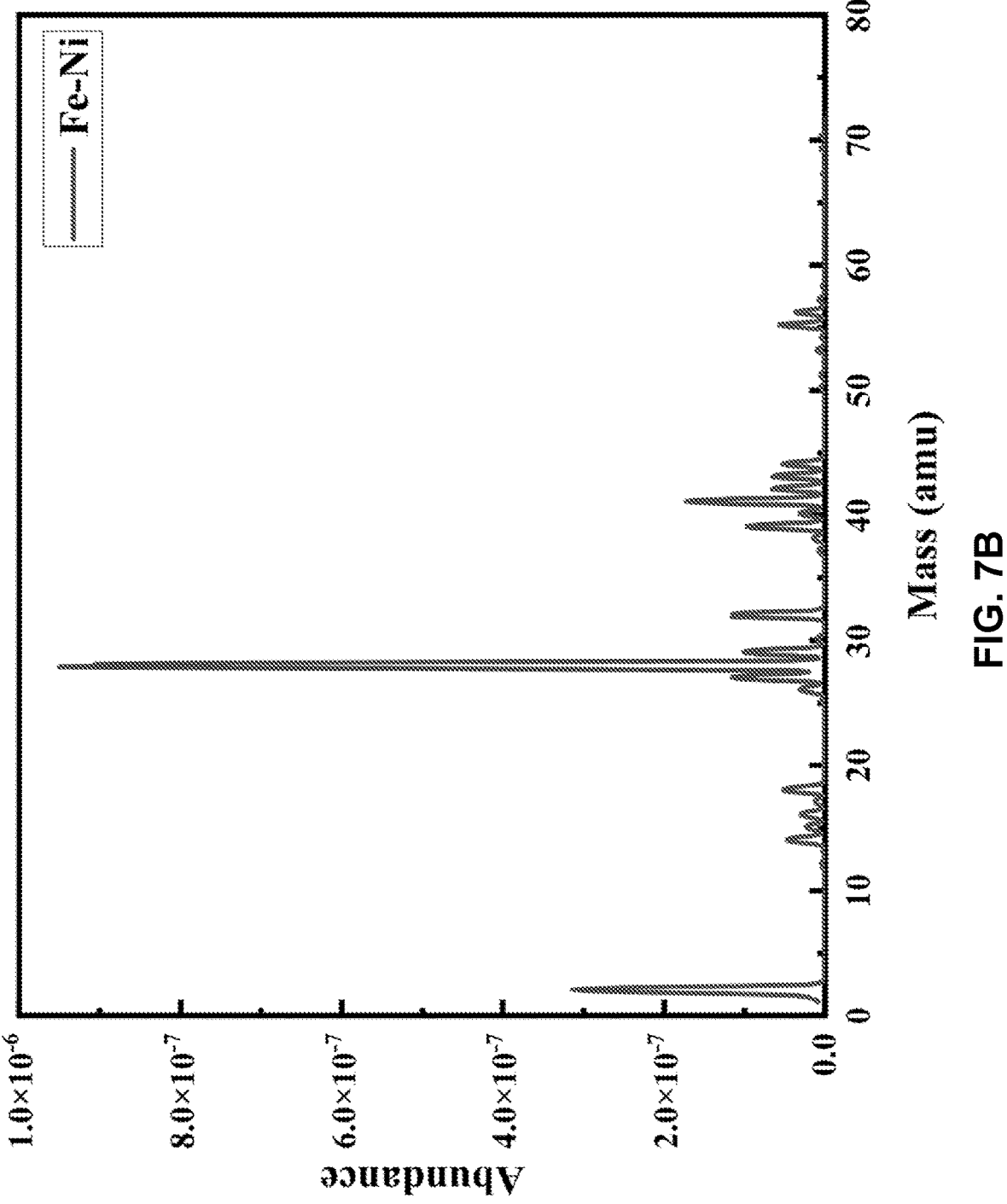

FIGS. 7A-7B show gas chromatograms by the RGA for the gas produced from RF-induced catalyzed depolymerizations in a 64 mT RF field for 2 h using the Fe—Pt—K-MFI (FIG. 7A) and the Fe—Ni (FIG. 7B) catalysts (115 mg cat: 1000 mg LDPE).

Figure 8A:
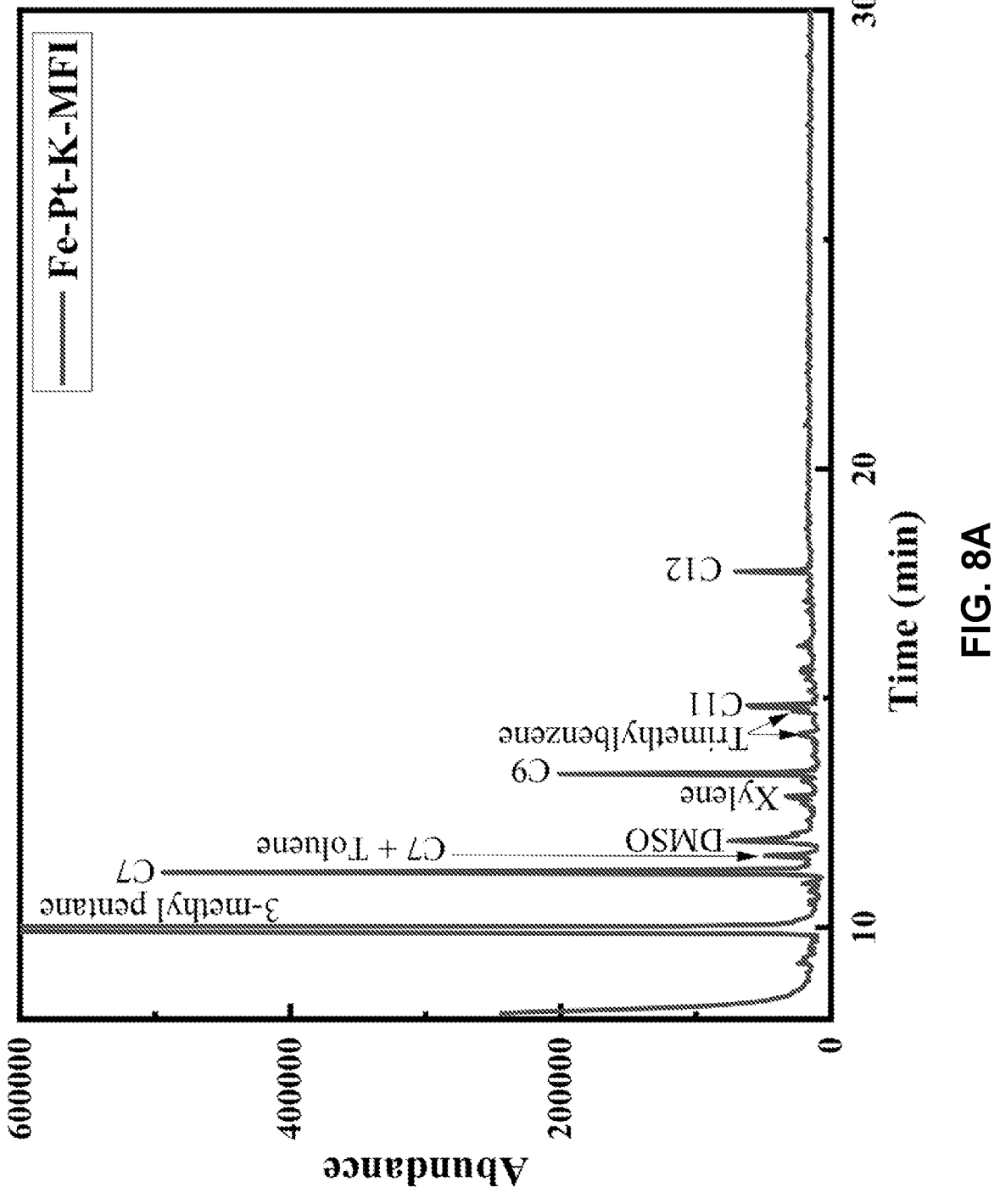
Figure 8B:
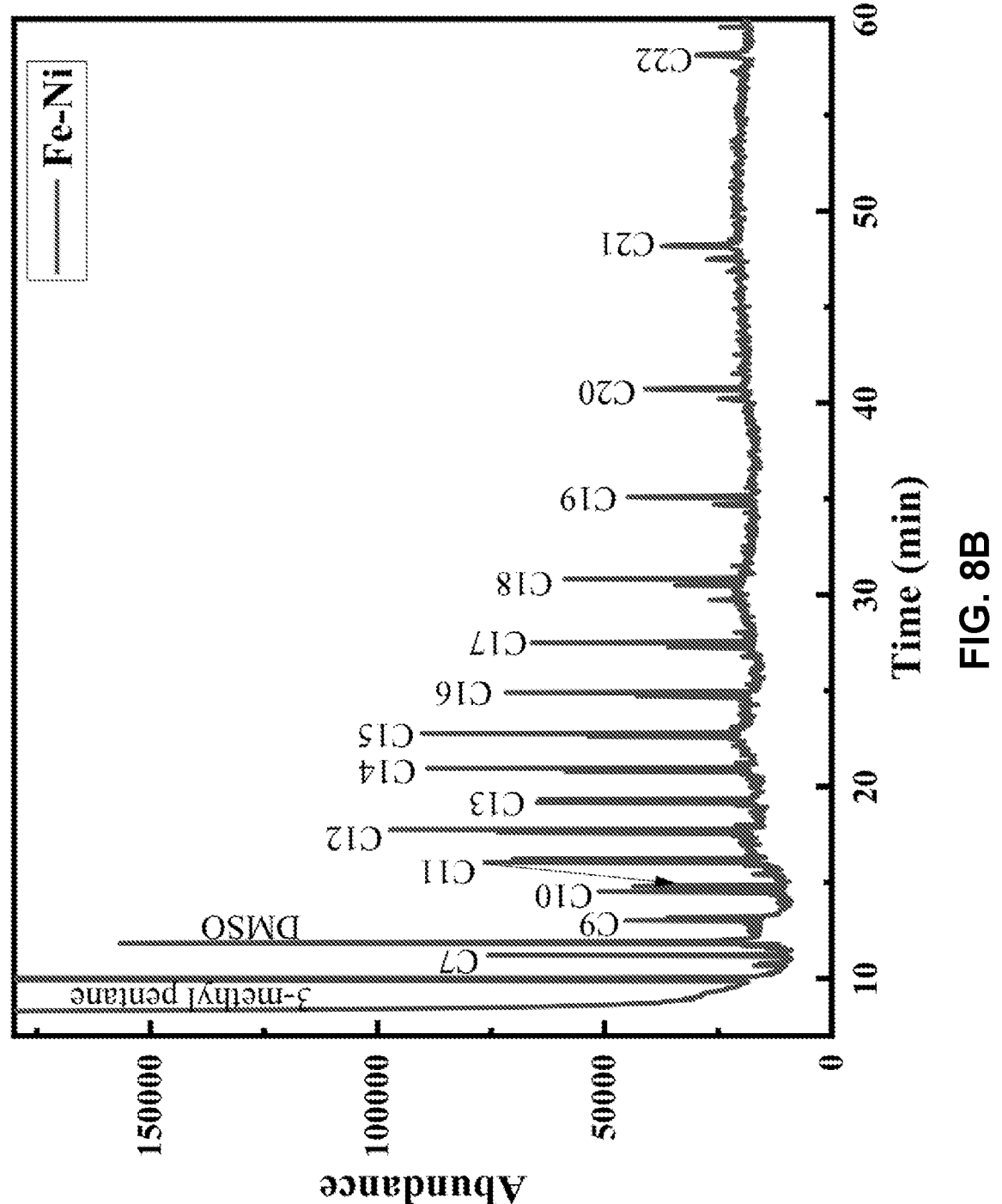

FIGS. 8A-8B show liquid product GC-MS analysis for RF-induced catalyzed depolymerizations in a 64 mT RF field for 2 h for the Fe—Pt—K-MFI (FIG. 8A) and the Fe—Ni (FIG. 8B) catalysts (115 mg cat:1000 mg LDPE).

Figure 9A:
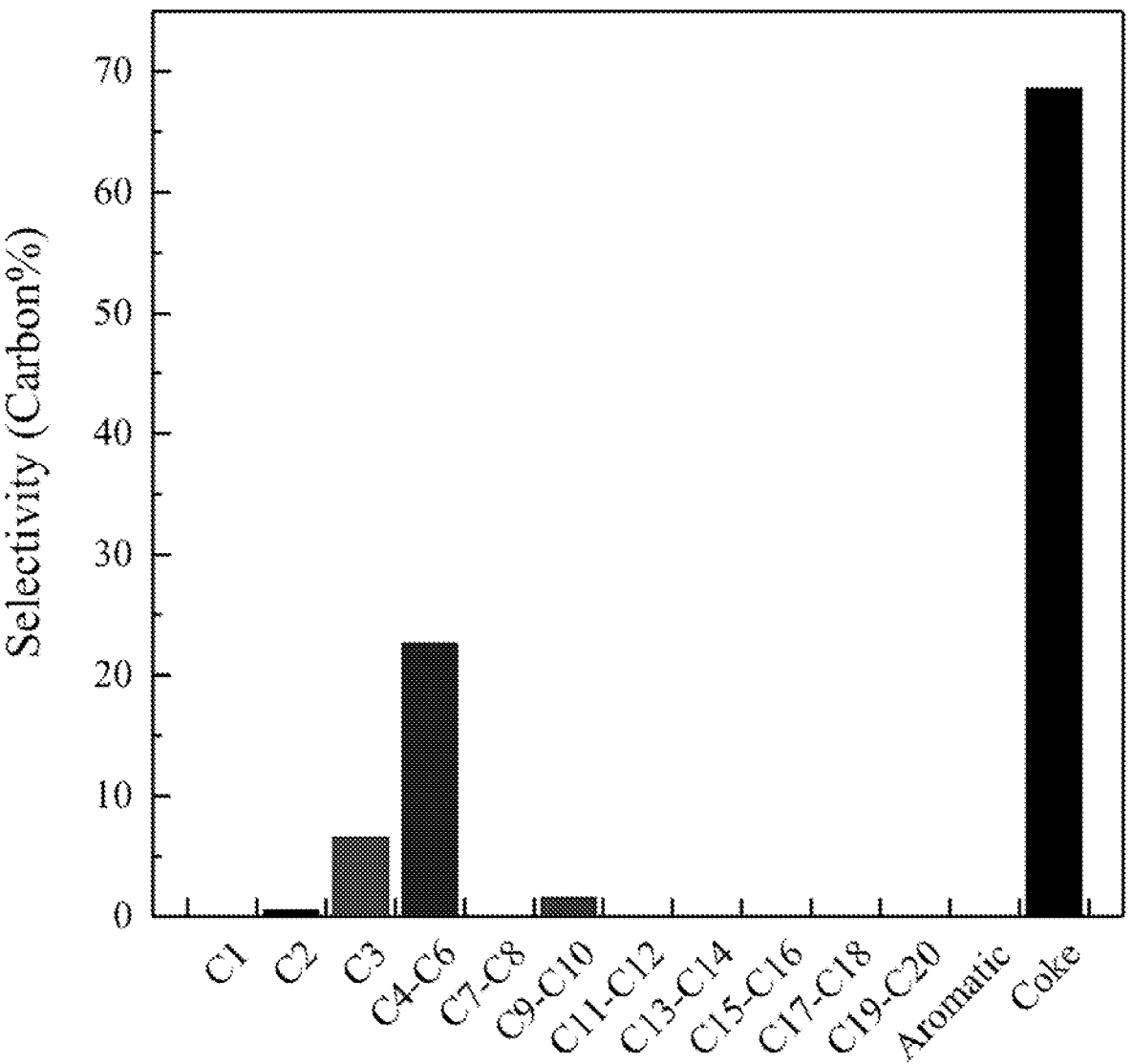
Figure 9B:
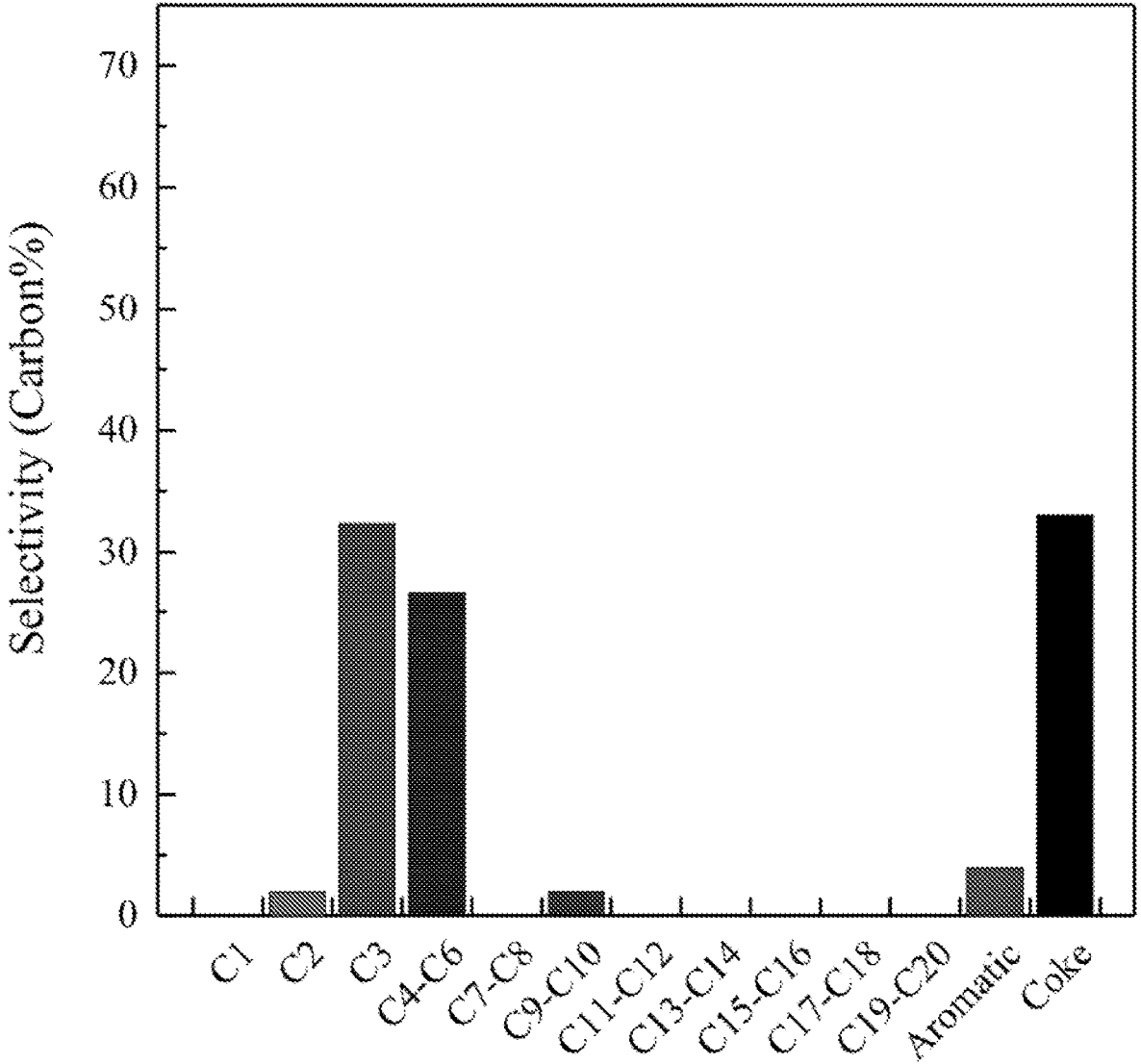

FIGS. 9A-9B show thermal depolymerization product selectivities on a carbon % basis run at FIG. 9A) 350° C. and FIG. 9B) 450° C.

Figure 10A:
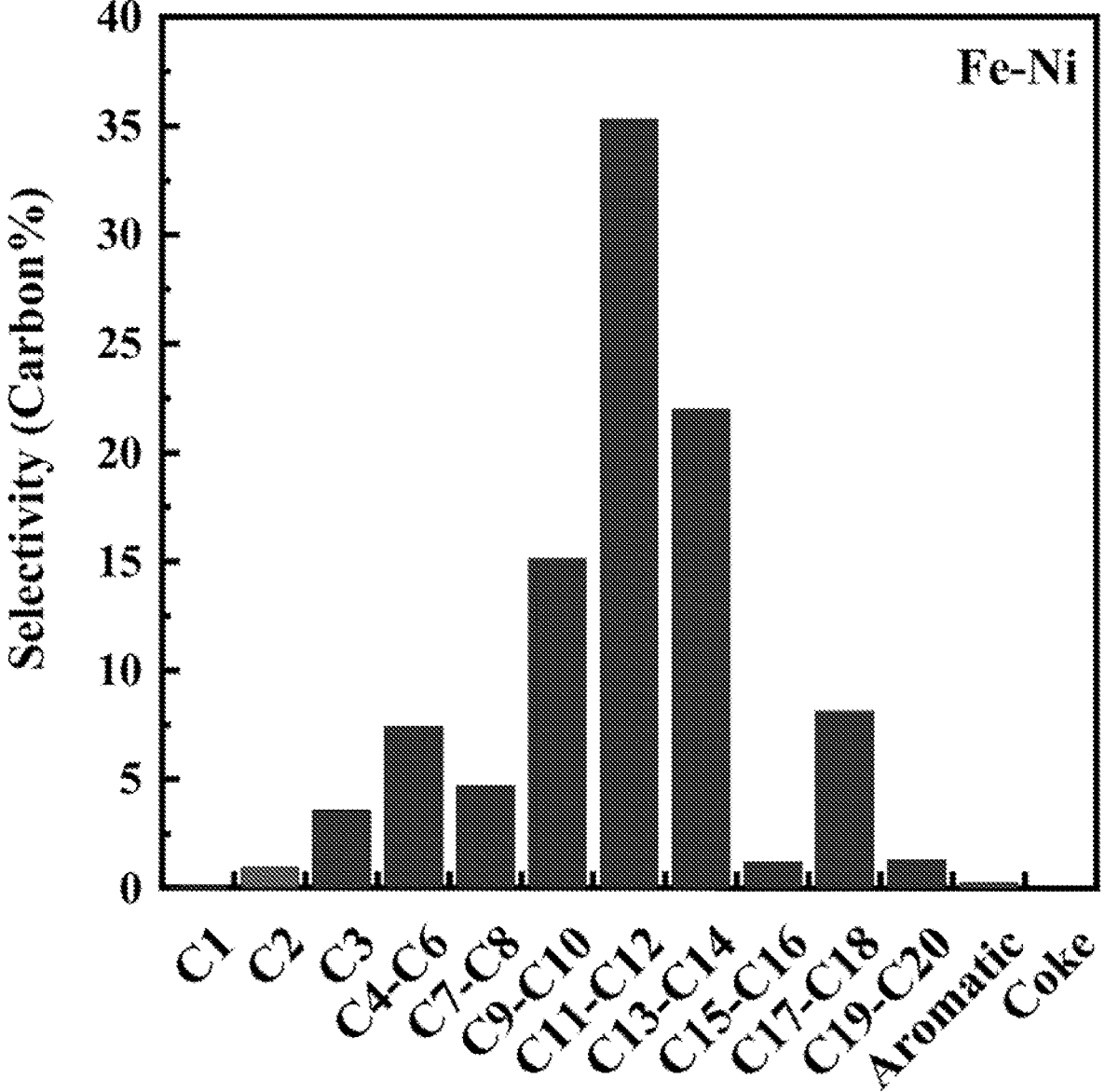
Figure 10B:
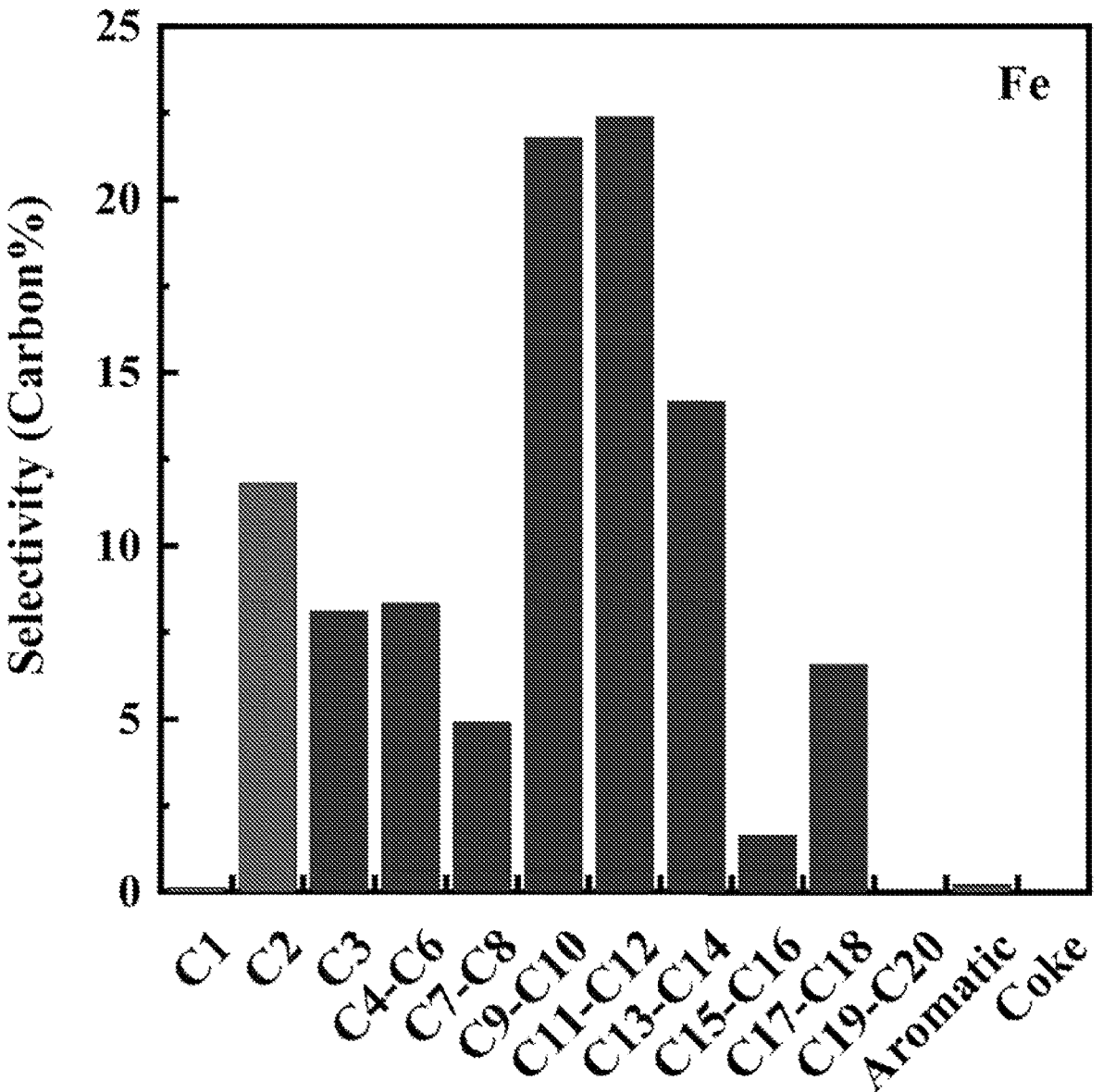

FIGS. 10A-10B show product selectivities for LDPE depolymerization over: FIG. 10A) Fe—Ni and FIG. 10B) Fe catalysts at a 200:1000 mg cat:polymer ratio under a 64 mT RF field for 2 h.

Figure 11A:
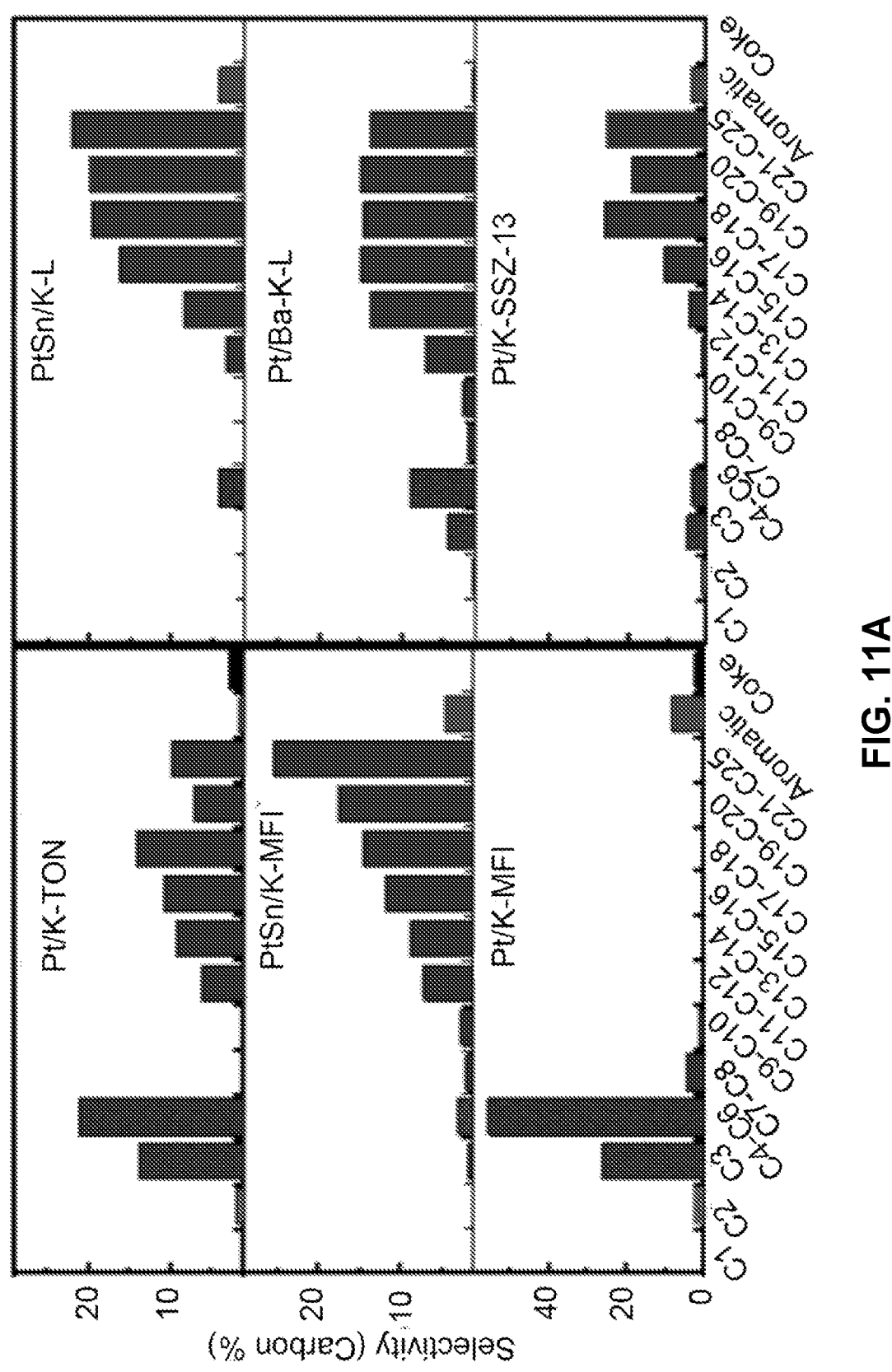
Figure 11B:
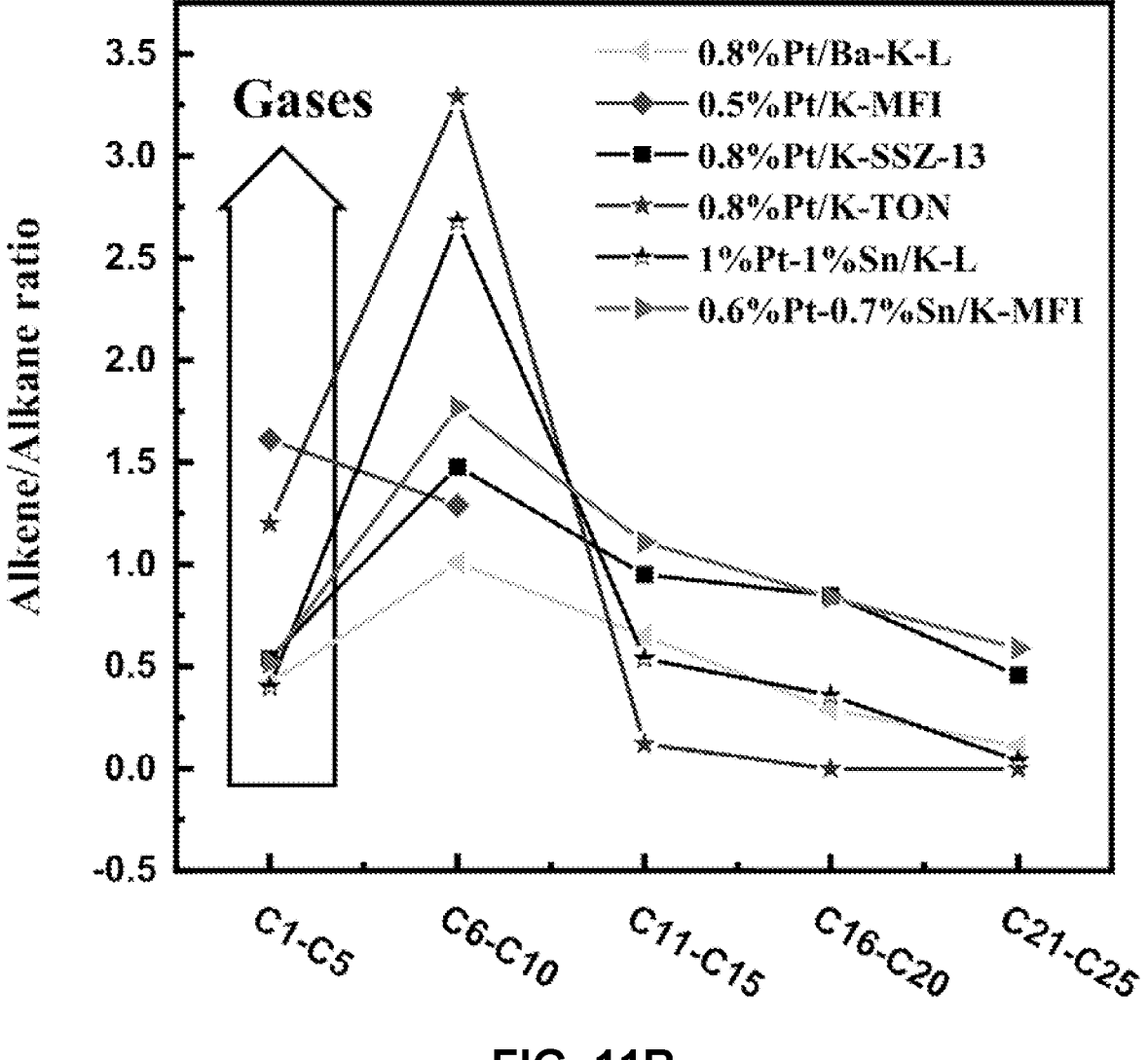

FIGS. 11A-11B show product selectivities and alkene/ alkane ratios for LDPE depolymerization using Pt-loaded zeolite catalysts at 500 A (54 mT). FIG. 11A: Product distributions on carbon mol % basis for LDPE depolymerization with Pt-loaded zeolite catalysts at 500 A (54 mT), 2 h. FIG. 11B: Alkene to alkane ratio of the product distribution.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein is a method for depolymerizing plastic, the method including at least the steps of:
    (a) providing a plastic material;
    (b) contacting the plastic material with at least one catalyst and at least one magnetic susceptor; and
    (c) induction heating the plastic material, catalyst, and magnetic susceptor using a radio frequency (RF) field.

In one aspect, the plastic material can be any common plastic including, but not limited to, low density polyethylene (LDPE), high density polyethylene (HDPE), polystyrene, polypropylene, polybutylenes, EPDM rubber, polyisoprene, styrene-butadiene rubber, poly(styrene-acrylonitrile) (SAN polymer), another plastic, copolymers thereof, or any combination thereof. In a further aspect, the plastic material can be an LDPE grocery bag.

In another aspect, useful catalysts disclosed herein can include crystalline aluminosilicates (zeolites), crystalline aluminophosphates, crystalline silicoaluminaphosphates, catalysts containing cerium oxide, or any combination thereof. In some aspects, these catalysts can be supported on catalytic aluminas, silicas, titanium oxides, magnesium oxides, activated carbons, or any combination thereof. In a further aspect, the catalyst can be doped with or otherwise contain a transition metal such as, for example, nickel, cobalt, manganese, molybdenum, vanadium, iron, platinum, palladium, tin, or any combination thereof. In one aspect, the magnetic susceptor can be $Fe_3O_4$.

In one aspect, the crystalline aluminosilicate, aluminophosphate, or silicoaluminaphosphate catalyst can be Linde Type-L (LTL), ZSM-5 (MFI) or another member of the ZSM family, Beta (BEA), Theta-1 (TON), SSZ-13, or any combination thereof. In another aspect, the cerium oxide-containing catalyst can include both cerium oxide and zirconium oxide. In one aspect, the catalyst can include platinum, such as, for example, that introduced through ion exchange, and can be selected from Pt/K-MFI, PtSn/K-MFI, Pt/Ba-K-L, PtSn/K-L, Pt/K-TON, Pt/K-SSZ-13, or any combination thereof. In one aspect, while K represents potassium ions and Ba represents barium ions, it should be understood that other commonly exchanged ions for zeolites can be substituted in the formulas listed herein, including alkali metals other than potassium (i.e., lithium, sodium, rubidium, cesium, and/or francium), alkaline earth metals other than barium (i.e., beryllium, magnesium, calcium, strontium, and/or radium), group 3 and group 4 ions of the periodic table (i.e., scandium, yttrium, lutetium, lawrencium, titanium, zirconium, hafnium, and/or rutherfordium), group 2b, 3b, and/or 4b ions of the periodic table (i.e., zinc, cadmium, mercury, boron, aluminum, gallium, indium, thallium, germanium, tin, and/or lead), or other transition metals including, but not limited to, nickel, platinum, and/or palladium. In a further aspect, combinations of two or more metals can also be considered to be disclosed in the same catalyst and can be introduced to the catalyst through a method including, but not limited to, ion exchange, wherein introduction of more than one metal can occur either sequentially or simultaneously.

In one aspect, the at least one catalyst can have an average pore diameter of from about 0.4 nm to about 0.6 nm, or of about 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, or about 0.6 nm, or a combination of any of the foregoing values, or a range encompassing any of the foregoing values. In another aspect, the at least one catalyst can have an average pore volume of from about 0.1 to about 0.3 cm$^3$/g, or from about 0.19 to about 0.27 cm$^3$/g, or of about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, or about 0.3 cm$^3$/g, or a combination of any of the foregoing values, or a range encompassing any of the foregoing values. In still another aspect, the at least one catalyst can have an average surface area of from about 50 to about 400 m$^2$/g, or of about 180 to about 250 m$^2$/g, or of about 50, 100, 150, 200, 250, 300, 350, or about 400 m$^2$/g, or a combination of any of the foregoing values, or a range encompassing any of the foregoing values.

In one aspect, the catalyst and magnetic susceptor can be present in a weight ratio of from about 2:1 to about 1:2, or of about 1:1, or of about 2:1, 2:1.1, 2:1.2, 2:1.3, 2:1.4, 2:1.5, 2:1.6, 2:1.7, 2:1.8, 2:1.9, 1:1, 1:1.1, 1:1.2, 1:1.3, 1:1.4, 1:1.5, 1:1.6, 1:1.7, 1:1.8, 1:1.9, about 1:2, or a combination of any of the foregoing values, or a range encompassing any of the foregoing values. In another aspect, a combined weight of the catalyst and magnetic susceptor and a weight of the plastic material can be present in a ratio of from about 1:10 to about 1:2, or of about 1:10, 1:9, 1:8, 1:7, 1:6, 1:5, 1:4, 1:3, or about 1:2, or a combination of any of the foregoing values, or a range encompassing any of the foregoing values.

In one aspect, the method disclosed herein can be conducted at low temperatures compared to current processes such as, for example, between about 200° C. and about 450° C., or at about 200, 250, 300, 350, 400, or about 450° C., or a combination of any of the foregoing values, or a range encompassing any of the foregoing values.

In another aspect, the RF field can have a current of from about 50 A to about 1000 A, or from about 300 A to about 600 A, or of about 50, 100, 150, 200, 250, 300, 350, 400, 450, 500, 550, 600, 650, 700, 750, 800, 850, 900, 950, or about 1000 A, or a combination of any of the foregoing values, or a range encompassing any of the foregoing values. In a further aspect, the RF field can have a field strength of from about 10 mT to about 100 mT, or of from about 32 mT to about 64 mT, or of about 10, 15, 20, 25, 30, 35, 40, 45, 50, 55, 60, 65, 70, 75, 80, 85, 90, 95, or about 100 mT, or a combination of any of the foregoing values, or a range encompassing any of the foregoing values. In still another aspect, the induction heating can be carried out for from about 30 min to about 48 h, or from about 1 h to about 24 h, or from about 1 h to about 5 h, or for about 30 min, 1, 2, 3, 4, 5, 6, 7, 8, 9, 10, 11, 12, 16, 20, 24, 28, 32, 36, 40, 44, or about 48 h, or a combination of any of the foregoing values, or a range encompassing any of the foregoing values. The disclosed method can be conducted as a batch process or a flow process and, in some aspects, does not require addition of H$_2$, a solvent, or both to the reaction vessel.

In some aspects, the catalyst is resistant to coking, poisoning from plastic additives and residues, or both. In one aspect, the plastic additives or residues can be antioxidants, flame retardants, plasticizers, food residue, green waste, another additive or residue, or any combination thereof.

In any of these aspects, the plastic material can depolymerize into C$_2$-C$_{20}$ alkanes or alkenes, cycloalkanes, cycloalkenes, polymerizable units, or any combination thereof. In a further aspect, depolymerization can proceed selectively depending on temperature, transition metal, and catalyst identity and amount, among other factors. In one aspect, at least 45% of the plastic material depolymerizes into C$_2$-C$_{20}$ alkanes or alkenes, cycloalkanes, cycloalkenes, polymerizable units, or any combination thereof, or at least 75% of the plastic material depolymerizes into C$_2$-C$_{20}$ alkanes or alkenes, cycloalkanes, cycloalkenes, polymerizable units, or any combination thereof.

In an aspect, the catalyst can be PtSn/K-L or Pt/K-SSZ-13 and at least 90% of the plastic material depolymerizes into C$_2$-C$_{20}$ alkanes or alkenes. In another aspect, the catalyst can be PtSn/K-L and from about 30% to about 50% of the C$_2$-C$_{20}$ alkanes or alkenes are C$_6$-C$_{20}$ alkanes or alkenes. In still another aspect, the catalyst can be Pt/K-MFI and from about 90% to about 99% of the C$_2$-C$_{20}$ alkanes or alkenes are C$_2$-C$_5$ alkanes or alkenes. In some aspect, the catalyst can be a ceria catalyst containing nickel and the plastic material depolymerizes into C$_7$-C$_{14}$ alkanes or alkenes.

In one aspect, the method produces less than 10 wt % coke on a carbon % basis, or less than 5 wt % coke on a carbon % basis. In another aspect, the method produces less than 7% one- and two-ring aromatic compounds on a carbon % basis, or less than 4% one- and two-ring aromatic compounds on a carbon % basis.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by," "comprising," "comprises," "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a magnetic susceptor," "a metal," or "an alkene," includes, but is not limited to, mixtures or combinations of two or more such magnetic susceptors, metals, or alkenes, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y.' The range can also be expressed as an upper limit, e.g. 'about x, y, z, or less' and should be interpreted to include the specific ranges of 'about x,' 'about y', and 'about z' as well as the ranges of 'less than x', less than y', and 'less than z'. Likewise, the phrase 'about x, y, z, or greater' should be interpreted to include the specific ranges of 'about x,' 'about y,' and 'about z' as well as the ranges of 'greater than x,' greater than y,' and 'greater than z.' In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a catalyst refers to an amount that is sufficient to achieve the desired improvement in the property modulated by the formulation component, e.g. achieving the desired level of plastic material conversion. The specific level in terms of wt % in a composition required as an effective amount will depend upon a variety of factors including the amount and type of plastic material, amount and type of metal included in the catalyst, length and duration of RF field exposure, and desired product distribution.

As used herein, the terms "optional" or "optionally" means that the subsequently described event or circumstance can or cannot occur, and that the description includes instances where said event or circumstance occurs and instances where it does not.

Unless otherwise specified, pressures referred to herein are based on atmospheric pressure (i.e. one atmosphere).

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Aspects

The present disclosure can be described in accordance with the following numbered aspects, which should not be confused with the claims.

Aspect 1. A method for depolymerizing plastic, the method comprising:
(a) providing a plastic material;
(b) contacting the plastic material with at least one catalyst and at least one magnetic susceptor; and
(c) induction heating the plastic material, catalyst, and magnetic susceptor using a radio frequency (RF) field.

Aspect 2. The method of aspect 1, wherein the plastic material comprises low density polyethylene (LDPE), high density polyethylene (HDPE), polystyrene, polypropylene, polybutylenes, EPDM rubber, polyisoprene, styrene-butadiene rubber, poly(styrene-acrylonitrile) (SAN polymer), copolymers thereof, or any combination thereof.

Aspect 3. The method of aspect 1 or 2, wherein the plastic material comprises a virgin polymer, a recycled plastic, or any combination thereof.

Aspect 4. The method of aspect 3, wherein the recycled plastic comprises an LDPE grocery bag.

Aspect 5. The method of any one of aspects 1-4, wherein the at least one catalyst comprises a crystalline aluminosilicate, aluminophosphate, or silicoaluminaphosphate catalyst, a cerium oxide-containing catalyst, or any combination thereof.

Aspect 6. The method of any one of aspects 1-5, wherein the at least one catalyst has an average pore diameter of from about 0.4 nm to about 0.6 nm.

Aspect 7. The method of any one of aspects 1-6, wherein the at least one catalyst has an average pore volume of from about 0.1 to about 0.3 cm$^3$/g.

Aspect 8. The method of aspect 7, wherein the at least one catalyst has an average pore volume of from about 0.19 to about 0.27 cm$^3$/g.

Aspect 9. The method of any one of aspects 1-8, wherein the at least one catalyst has an average surface area of from about 50 to about 400 m$^2$/g.

Aspect 10. The method of aspect 9, wherein the at least one catalyst has an average surface area of from about 180 to about 250 m$^2$/g.

Aspect 11. The method of any one of aspects 5-10, wherein the catalyst is doped with at least one metal or metalloid.

Aspect 12. The method of aspect 11, wherein the at least one metal or metalloid comprises potassium, barium, lithium, sodium, rubidium, cesium, francium, beryllium, magnesium, calcium, strontium, radium, scandium, yttrium, lutetium, lawrencium, titanium, zirconium, hafnium, rutherfordium, zinc, cadmium, mercury, boron, aluminum, gallium, indium, thallium, germanium, tin, lead, platinum, palladium, nickel, or any combination thereof.

Aspect 13. The method of any one of aspects 5-12, wherein the crystalline aluminosilicate, aluminophosphate, or silicoaluminaphosphate catalyst comprises Linde Type-L (LTL), ZSM-5 (MFI) or another member of the ZSM family, Beta (BEA), Theta-1 (TON), SSZ-13, or any combination thereof.

Aspect 14. The method of any one of aspects 5-12, wherein the cerium oxide-containing catalyst comprises cerium oxide and zirconium oxide.

Aspect 15. The method of any one of aspects 11-14, wherein the at least one metal comprises a transition metal.

Aspect 16. The method of aspect 15, wherein the transition metal comprises nickel, platinum, palladium, tin, or any combination thereof.

Aspect 17. The method of any one of aspects 13-16, wherein the catalyst comprises Pt/K-MFI, PtSn/K-MFI, Pt/Ba-K-L, PtSn/K-L, Pt/K-TON, Pt/K-SSZ-13, or any combination thereof.

Aspect 18. The method of any one of the preceding aspects, wherein the at least one magnetic susceptor comprises Fe$_3$O$_4$.

Aspect 19. The method of any one of the preceding aspects, wherein the catalyst and magnetic susceptor are present in a weight ratio of from about 2:1 to about 1:2.

Aspect 20. The method of any one of the preceding aspects, wherein the catalyst and magnetic susceptor are present in a weight ratio of about 1:1.

Aspect 21. The method of any one of the preceding aspects, wherein a combined weight of the catalyst and magnetic susceptor and a weight of the plastic material are present in a ratio of from about 1:10 to about 1:2.

Aspect 22. The method of any one of the preceding aspects, wherein a combined weight of the catalyst and magnetic susceptor and a weight of the plastic material are present in a ratio of about 1:5.

Aspect 23. The method of any one of the preceding aspects, wherein the induction heating raises a temperature of the plastic material, catalyst, and magnetic susceptor to from about 200° C. to about 450° C.

Aspect 24. The method of aspect 23, wherein the temperature is from about 340° C. to about 375° C.

Aspect 25. The method of any one of the preceding aspects, wherein the RF field has a current of from about 50 A to about 1000 A.

Aspect 26. The method of any one of the preceding aspects, wherein the RF field has a field strength of from about 10 mT to about 100 mT.

Aspect 27. The method of aspect 23, wherein induction heating is carried out for from about 30 minutes to about 48 hours.

Aspect 28. The method of any one of the preceding aspects, wherein the method is conducted as a batch process or as a flow process.

Aspect 29. The method of any one of the preceding aspects, wherein the method does not require addition of H$_2$, a solvent, or both.

Aspect 30. The method of any one of the preceding aspects, wherein the catalyst is resistant to coking, poisoning from plastic additives and residues, or both.

Aspect 31. The method of aspect 30, wherein the plastic additives and residues comprise antioxidants, flame retardants, plasticizers, food residue, green waste, or any combination thereof.

Aspect 32. The method of any one of the preceding aspects, wherein the plastic material depolymerizes into C$_2$-C$_{20}$ alkanes or alkenes.

Aspect 33. The method of aspect 32, wherein at least 45% of the plastic material depolymerizes into $C_2$-$C_{20}$ alkanes or alkenes.

Aspect 34. The method of aspect 32, wherein at least 75% of the plastic material depolymerizes into $C_2$-$C_{20}$ alkanes or alkenes.

Aspect 35. The method of aspect 32, wherein the catalyst comprises PtSn/K-L or Pt/K-SSZ-13 and at least 90% of the plastic material depolymerizes into $C_2$-$C_{20}$ alkanes or alkenes.

Aspect 36. The method of aspect 32, wherein the catalyst comprises PtSn/K-L and wherein from about 30% to about 50% of the $C_2$-$C_{20}$ alkanes or alkenes are $C_6$-$C_{20}$ alkanes or alkenes.

Aspect 37. The method of aspect 32, wherein the catalyst comprises Pt/K-MFI and wherein from about 90% to about 99% of the $C_2$-$C_{20}$ alkanes or alkenes are $C_2$-$C_5$ alkanes or alkenes Aspect 38. The method of any one of the preceding aspects, wherein at least a portion of the plastic material depolymerizes into polymerizable units.

Aspect 39. The method of any one of aspects 11-38, wherein the catalyst comprises a ceria catalyst comprising nickel and wherein the plastic material depolymerizes into $C_7$-$C_{14}$ alkanes or alkenes.

Aspect 40. The method of any one of the preceding aspects, wherein the method produces less than 10 wt % coke on a carbon % basis.

Aspect 41. The method of any one of the preceding aspects, wherein the method produces less than 5 wt % coke on a carbon % basis.

Aspect 42. The method of any one of the preceding aspects, wherein the method produces less than 7% one- and two-ring aromatic compounds on a carbon % basis.

Aspect 43. The method of any one of the preceding aspects, wherein the method produces less than 4% one- and two-ring aromatic compounds on a carbon % basis.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Methods

Catalyst Synthesis

Three candidate zeolites already in their $H^+$ forms were ion-exchanged first to the $K^+$ and then the $Ni^{2+}$ forms using 0.1 M Ni($CH_3COO)_2$: Beta (BEA), Linde Type-L (LTL) and MFI (ZSM-5, ACS LLC). The exchanged zeolites were dried at 400° C. and calcined in flowing air at 500° C. The fully exchanged zeolites would contain 2.4 wt % (ZSM-5, Si/Al=20) or 5.0 wt % Ni (BEA, Si/Al=8). An additional two other silicates (ferrierite, FER, and the mesoporous silica SBA-16 were instead impregnated with Ni($NO_3)_2 \cdot 6H_2O$, because for these there are few available exchange sites. The silicates were impregnated dropwise to 5 wt % NiO, dried at 100° C., and calcined at 500° C. in flowing air. An overloaded ZSM-5 (Ni2-ZSM-5) was prepared via dropwise impregnation (to 20 wt % Ni) and calcined similarly. Finally, a Pt(0.5 wt %)-K-ZSM-5 was made from a K+-exchanged ZSM-5 (Si/Al=29, Zeolyst lot 5534G-1597-94) by contacting the zeolite overnight with dilute aqueous platinum diaminodinitrite at pH=10. The solution was slowly evaporated at 120° C., followed by a pulse reduction (H2 at 400° C.) to give 25% Pt dispersion at RT using $H_2$ chemisorption.

A Ni/$CeO_2$/$ZrO_2$ (Ni—Ce—Zr, 4.7 wt % Ni, 2:1 Ce:Zr atomic ratio) catalyst was synthesized previously by a molten salt/urea deposition method (80° C. from 0.3 M urea, Ni($NO_3)_2 \cdot 6H_2O$ solution, 30:1 solution/solid by weight), then reduced in 5% $H_2$ at 750° C. for 6 h. Nanoparticulate $Fe_3O_4$(Alfa Aesar, 97%, 50-100 nm, 20-50 $m^2$/g) was used as received. A Ni/$Fe_3O_4$(Fe—Ni, 2.4 wt % Ni) catalyst was made from these nanoparticles by urea deposition of Ni, dried under vacuum at 60° C., then reduced in 5% $H_2$ at 500° C. for 12 h. A 20 wt % Ni on a commercial Ce—Zr—Al support (Ni20-CZA40, from PIDC CZA-40, 1:1 Ce:Zr atomic ratio, 40 wt % $Al_2O_3$) was prepared by two successive incipient wetness impregnations separated by 100° C. dryings, then reduced in 5% $H_2$ at 750° C. for 6 h.

A $Fe_3O_4$@$CeO_2$ 5:1 (molar) core-shell mixed oxide was synthesized following a modified method of Jiang et al. to produce the $Fe_3O_4$ core. The $CeO_2$ oxide shell was then added by adapting the hydrothermal method of Wei et al. The particles are washed with ethanol/water after both synthesis steps, instead of drying under $N_2$, to avoid oxidation to $Fe_2O_3$. Finally, 5.8 wt % Ni was added by the urea deposition method and dried and reduced the same way as Fe—Ni to give catalyst Fe—Ce—CS—Ni.

Thermal Reaction Experiments

Both the $H^+$- and $Ni^{2+}$-forms of silicate and zeolite catalysts were used in these experiments. For each run, ~10-20 mg of catalyst and a typical commercial HDPE (ExxonMobil BA-50 HDPE copolymer, pelletized) were ground together at a 1:1 mass ratio and added to an $Al_2O_3$ sample cup in a TGA/DSC (TA SDT-600). From previous work it was known that the polymer would be both dry and molten by ~190° C. The temperature was ramped from 50° C. at 10° C. per min to 190° C., then 5° C. to 350° C. and held for 900 min under a 100 mL/min $N_2$ flow.

RF- and Thermally-Activated Batch Reaction Experiments

A schematic of the reactor is shown in FIG. 6. Briefly, 200 mg of the catalyst/$Fe_3O_4$ powder (1:1 wt ratio) was mixed with 1 g LDPE polymer (Alfa, 924 kg/$m^3$, melting point 105-115° C.). The mixture was loaded in a glass reactor, purged with $N_2$, and either exposed to an RF field (300-600 A, 32-64 mT equivalent) or immersed in a heated sand bath (heat supplied by a resistance heater/temperature controller), in both cases for 2 h. A temperature vs. magnetic field calibration was performed to correlate the induction heating-induced temperatures. The reaction vessel cooled for 30 min prior to collection of gas/liquid products. To calibrate the temperature range in the RF-activated experiments, the $Fe_3O_4$ nanoparticles were mixed with 1-octadecane (b.p. 315° C.), n-tetracosane (b.p. 391° C.), or NaCl:$ZnCl_2$ salt mixture (m.p. ~250-800° C. depending on salt composition). Alternatively, the $Fe_3O_4$ powders were mixed with hydrothermally grown $YVO_4$:$Eu^{3+}$ (3 mol %) nanoparticles (3:1 mixture). Briefly, 1.14 mmol of Y($NO_3)_3 \cdot 6H_2O$ and 0.6 mmol of $Na_3C_6H_5O_7 \cdot 2H_2O$ were added dropwise into 0.06 mmol of Eu($NO_3)_3 \cdot 6H_2O$ dissolved in 50 mL $HNO_3$ solution (12 mM) with continuous stirring for 10 min followed by 1.2 mmol of $NH_4VO_3$ under vigorous stirring. A 1 M NaOH solution was added dropwise until a pH of 9 and the solution was transferred into a 20 mL Teflon lined autoclave and reacted at 180° C. for 24 h. After naturally cooling, the resultant precipitate was collected and washed with ethanol/water before drying overnight at 100° C. The photoluminescence intensity was calibrated using a Linkam heating stage connected to an Edinburgh FLS1000 spectrometer. The in-situ temperature measurements were collected by placing the $Fe_3O_4/YVO_4$ mixture in a quartz holder in the center of the RF coil and exposed to the magnetic fields for 2 min prior to collection of the PL spectra ($\lambda_{ex}$=397 nm, $\lambda_{em}$=575-675 nm).

Product Analysis

The gas atmosphere was sampled during the experiment and analyzed by injection into an SRS RGA200 residual gas analyzer operating in selective ion mode at the parent m/e values. Pressure-ion count calibration was based on injection of standards. The total weight change of the system was used to estimate the conversion to light gases. Other depolymerization products were extracted from the remaining polymer/catalyst mixture with 90/10 (vol %) 3-methylpentane/DMSO solvent blend for 7 d. The liquid products were then analyzed by GC-MS on an Agilent 6890 (100 m×0.25 mm SPB-1 column). The liquid conversion was estimated from the weight change upon drying a sample of catalyst/product mass under vacuum at 170° C. for 7 d. Coke amounts were determined by temperature-programmed oxidation (TPO) in air, 50-250° C., 10° C./min, hold 60 min, 10° C./min to 420° C., hold 40 min, 10° C./min to 650° C., hold 60 min. The product selectivity (Si) is defined as:

$$(S_i) = \frac{(100)(\text{mol }\%_i)(C_i)}{\sum (\text{mol }\%_i)(C_i)} \qquad \text{Eq. 1}$$

14

Example 2: Results and Discussion

Thermal Reactions

Initially, the catalysts were thermally screened (TGA/DSC) using HDPE/catalyst blends. Catalysts were characterized based on their overall reaction rates (mass change, Eq. 2) and heat flux (indicative of selectivities to lower MW products, Eq 3). The results of these screening experiments are shown in Table 1. A blank run (no catalyst) showed no polymer weight loss at >150° C., with minor losses at lower temperatures due to drying. The heat flux is calculated for all times after the polymer melting is complete and the DSC baseline is smooth (>200° C.). As almost all the weight loss occurred during the 350° C. hold (FIG. 1A), the rates can be considered typical of that temperature.

$$\frac{\Delta PE_{wt}}{PE_{MW}(CAT_{wt}*\Delta t)}\left(\frac{1000}{60}\right) = \text{Reaction Rate} \qquad \text{Eq. 2}$$

$$\frac{\int H\,dt}{PE_{wt}}(60) = \text{total heat/wt} \qquad \text{Eq. 3}$$

TABLE 1

Depolymerization rate and selectivity data (TGA/DSC) and morphological characterization for various zeolite/metal oxide catalysts.

| Catalyst | $10^4$ × Rate (mmol gcat$^{-1}$ s$^{-1}$) | Heat/Wt Poly (J/g) | Surface Area (m$^2$/g) | Pore Volume, cm$^3$/g |
|---|---|---|---|---|
| Ni-BEA | 0.79 | −228 | 480 | 0.28 |
| H-BEA | 3.3 | −1720 | | |
| Ni-ZSM-5 | 7.2 | 4840 | 310 | 0.36 |
| Ni(0)-ZSM-5 | 3.7 | 5960 | | |
| Ni2-ZSM-5 | 7.1 | 410 | 300 | 0.22 |
| H-ZSM-5 | 2.9 | 8190 | 320 | 0.32 |
| Ni-FER | 0.11 | −254 | 49 | 0.17 |
| H-FER | 3.0 | 724 | | |
| Ni-LTL | 1.7 | −5260 | 550 | 0.31 |
| H-LTL | 4.1 | 820 | | |
| Ni-SBA | 3.1 | 5360 | 480 | 0.37 |
| Fe$_3$O$_4$ | 0.81 | 7720 | 33 | 0.11 |
| Ni—Ce—Zr | 0.32 | −3250 | 26 | 0.12 |
| Fe—Ce—CS—Ni | 0.71 | −1790 | 37 | 0.16 |
| Fe—Ni | 0.24 | 318 | 4.9 | 0.025 |
| Ni20-CZA40 | 1.3 | 1840 | 79 | 0.49 |
| Pt—K-ZSM-5 | 7.1 | −2580 | 370 | 0.25 |
| Pt complex | 63 | 9820 | N/A | | where $C_i$ is the number of carbons in the compound

Catalyst Characterization

Surface areas and pore volumes were measured by the BET method (Micromeritics ASAP 2020). TGA/DSC of 1-propylamine (1-PA) was employed to titrate the Brønsted sites, as discussed by Gorte and Price and Dooley, based on desorption temperature shifts and decreases in adsorbed amounts associated with replacement of H$^+$ by Ni$^{2+}$.

This method assumes that all low MW products (<C20) will be vaporized in the N$_2$ flow. Therefore, it is hypothesized that the measured weight loss is proportional to the rate of depolymerization to usable products. Additionally, the heat per weight of polymer is a measure of the overall, average heat of the reactions. While it is not possible to distinguish the formation of light gases, aromatics or coke from other products based on the average heat flux, this metric can distinguish endothermic from exothermic reactions. The highly endothermic reactions are expected to correspond to a mixture rich in light alkenes such as ethylene ($\Delta H_{depoly}$=3825-3875 J/g). Less endothermic values correspond to a mixture richer in mid-range alkenes (the heat of reaction for $C_{20}H_{40}$ to two mols of decene is 640 J/g). However, exothermic values suggest the formation of aromatics/coke and the concomitant hydrogenation to alkanes. Additionally, there are enthalpy changes associated with the catalyst itself (phase transformations, surface reconstructions, oxidation, etc.) that affect the measured heat flux.

An initial screening of the reaction rates shows that the Ni-modified ZSM-5 catalysts demonstrate much higher activities than the other zeolites. It appears that a coordinated Ni (Ni-ZSM-5) structure plays an important role in the decomposition process. Reducing this catalyst (in 5% $H_2$ at 350° C., Ni(0)-ZSM-5 in Table 1), significantly decreased the activity (by ~50%). The higher heat flux of the reduced sample is likely due to some oxidation of the Ni species during the TGA/DSC experiment. Deposition of extra Ni onto the catalysts (Ni2-ZSM-5) has negligible impact on the overall reaction rate while significantly decreasing the heat flux, suggesting the formation of more alkanes or aromatics. On the other hand, the Pt exchanged zeolite (Pt—K-ZSM-5) exhibits high, exothermic reaction rates. In addition to coking or aromatics formation, Pt-zeolite catalysts are well known for their hydrocracking capability (exothermic). The other zeolites gave lower reaction rates ($<3\times10^{-4}$ mmol $g^{-1}$ $s^{-1}$) with exothermic or slightly endothermic heat fluxes ($<1000$ J $g^{-1}$) for the $H^+$- and $Ni^{2+}$-modified forms, except for Ni-SBA. Conversely, the reaction rates (and surface area) for the metal oxide catalysts were low. However, the endothermic heat flux for the Fe3O4 catalyst was greater than all but the Pt organometallic complex and H-ZSM-5. The high endothermic flux indicates the formation of some heavy non-volatile hydrocarbons.

Figure 1A:
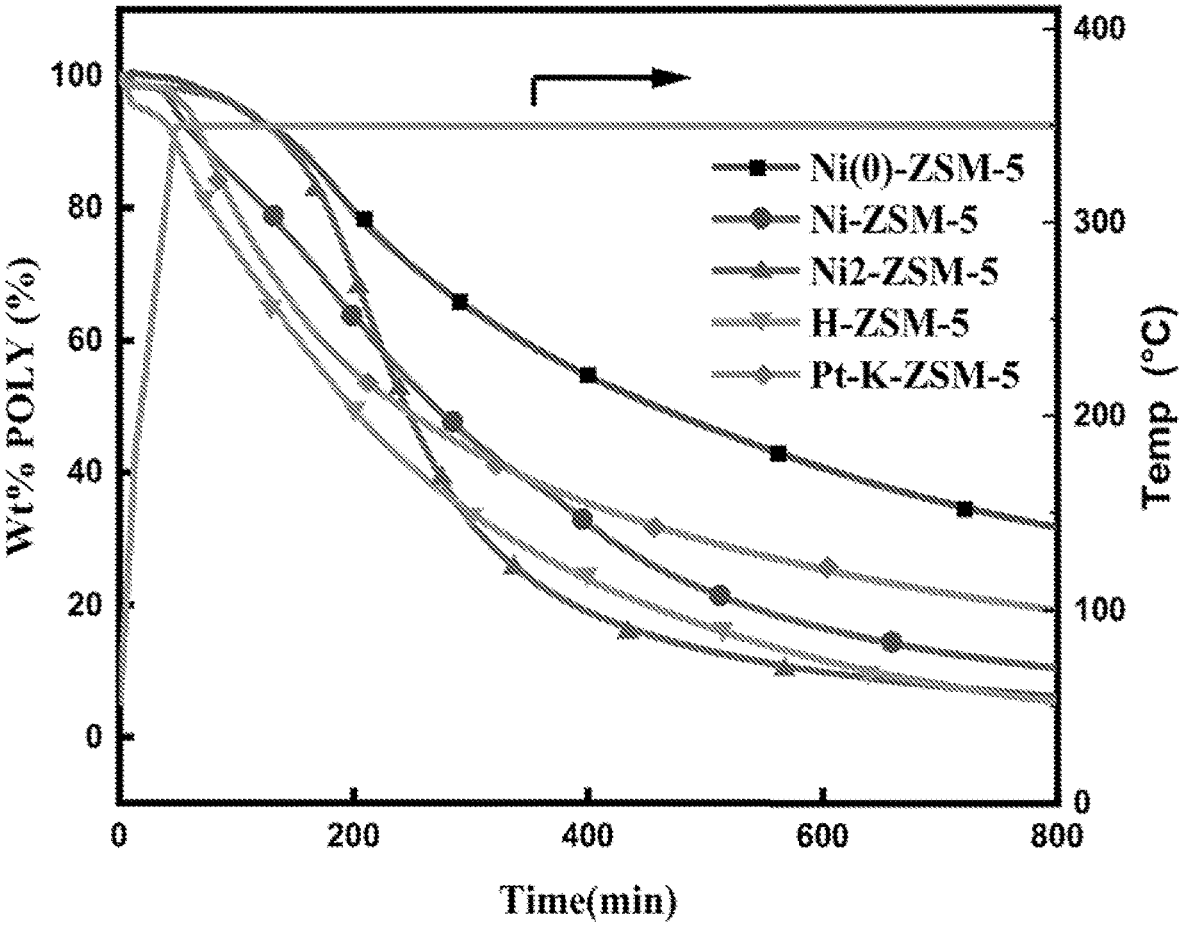
FIGS. 1A-1C show weight loss and rate variation curves (FIG. 1A) HDPE wt loss curves over modified ZSM-5 catalysts heated to 350° C. as a function of time (FIG. 1B) Temporal rate variation in TGA/DSC analyses for the zeolites catalysts (FIG. 1C) Temporal rate variation in TGA/ DSC analyses for the metal oxide catalysts.
Figure 1B:
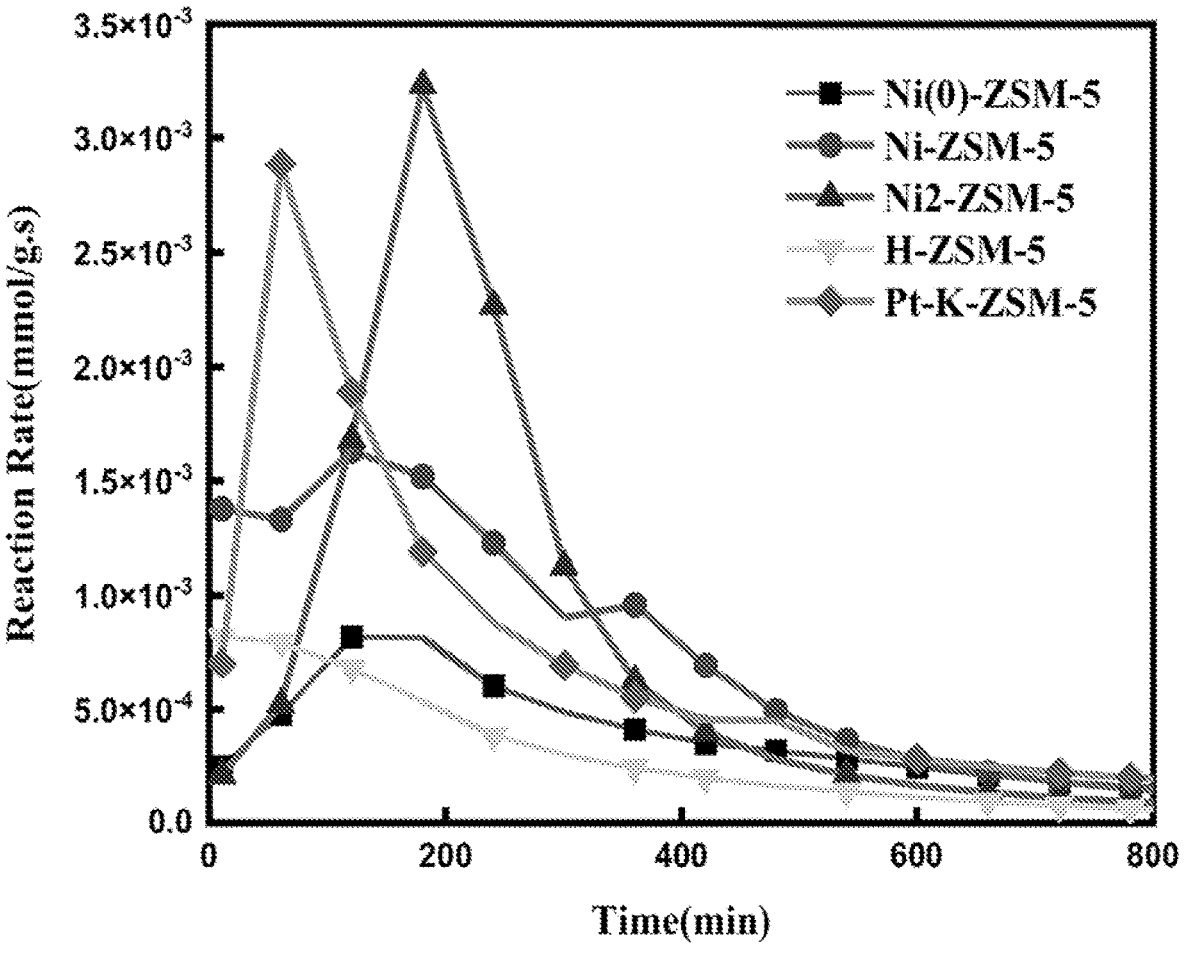
Figure 1C:
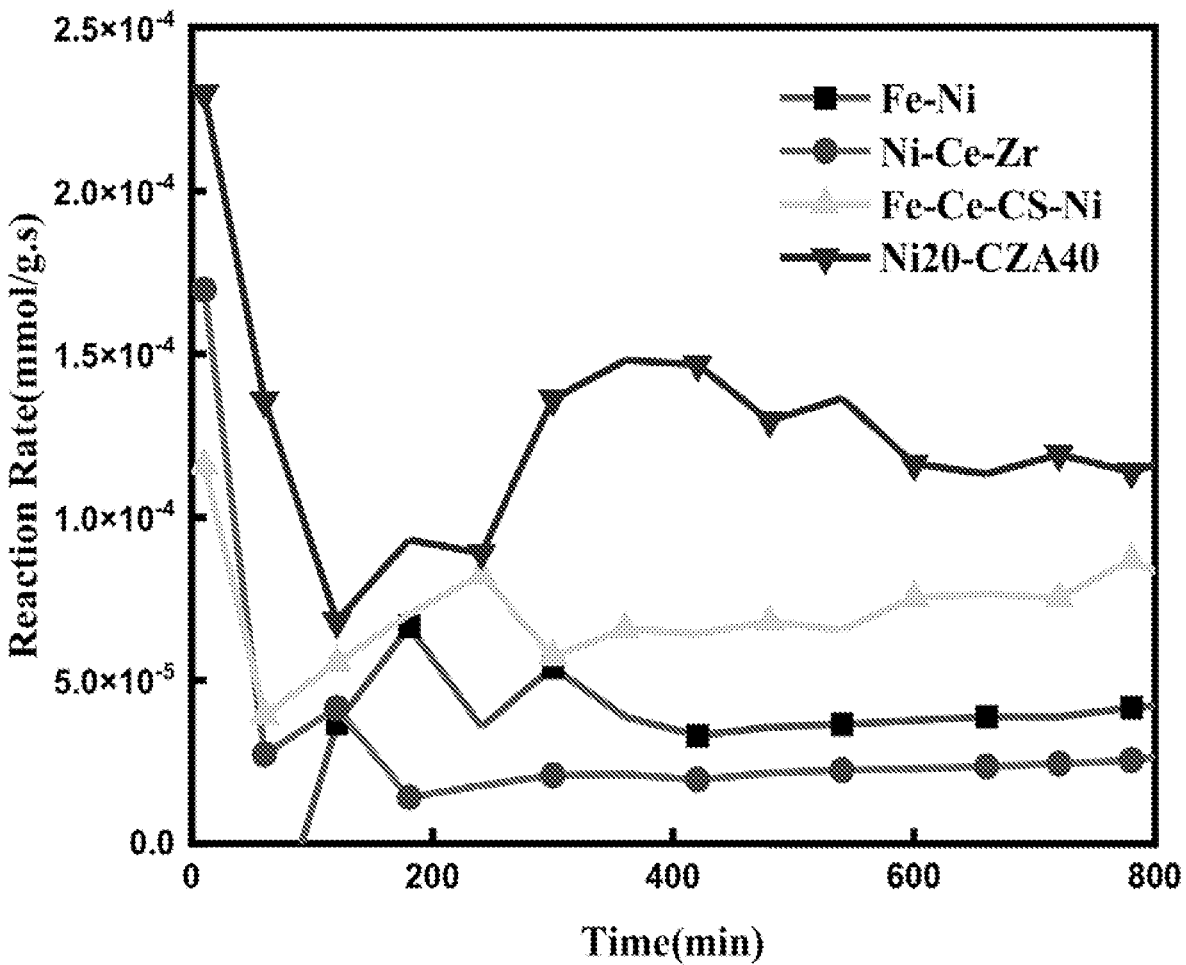

To understand the depolymerization process over the ZSM-5 and metal oxide catalysts throughout the experiment, time-dependent reactions rates (FIGS. 1B-1C) were extracted. The polymer conversion at any time is approximately 100-wt % polymer (FIG. 1A). The rates for the ZSM-5 catalysts (FIGS. 1B-1C) build to a maximum as the temperature approaches 350° C. then decrease with time. Alternatively, an initial decrease (Ce-based oxides) or increase (Fe—Ni) in reaction rates for the oxides is attributed to the removal of surface hydroxyls or substrate oxidation, respectively. The decrease in rate overtime is partly due to the consumption of polymer but also possibly due to coke formation and pore blockage. Without larger-scale experiments and spent catalyst characterizations, these two possibilities cannot be distinguished. However, the heat fluxes are relatively stable for all catalysts, suggesting a continuous depolymerization process. From these experiments, it is seen that the exchanged zeolites are more active after an initial induction period, a period which can be attributed to slow polymer pore diffusion. These diffusional resistances are less for the large-pore metal oxides; however, the decreased reaction rates for the metal oxides compared to the zeolites are in keeping with the relative surface areas (10-fold decrease for the Ce-based oxides compared to the zeolites, Table 1). To obtain a Ni—$CeO_2$ based catalyst with somewhat higher surface area and pore volume, a commercial support containing 40 wt % $Al_2O_3$(Fe-Ni20-CZA40) was used, showing higher reaction rates (2-5x) than the in-house catalysts.

As a comparison, the activity of a homogeneous Pt catalyst (Pt(divinyltetramethylsiloxane), 2.25 wt % in xylene) was measured. One would expect the soluble homogeneous Pt catalyst to give even higher rates due to more intimate contacting between the polymer and catalyst and the overall cracking activity of Pt compared to Ni. The xylene does not impact the reaction rate or heat flux calculations since the solvent evaporates (b.p. 139° C.) before the polymer melting point is reached. The average reaction rate is much higher than the heterogeneous catalysts (Table 1). At longer times, the rates for the Pt complex are comparable to Ni-ZSM-5 based catalysts. Regardless of the catalyst, the observed reaction rates would require long reaction times or large quantities of catalyst (50,000 kg of Ni-ZSM-5 per kg/s polymer reacted) to be commercially viable. As such, alternative approaches must be explored to enhance the reaction rates.

RF-Activated Reactions

Induction heating was employed as an alternative to thermal heating due to the increased heat transfer efficiencies and the ability to locate the heat at the active catalyst site. Before the depolymerization reactions could proceed, it was necessary to calibrate the reaction temperature. To calibrate these field-dependent temperatures, the $Fe_3O_4$ powder was mixed with various heavy hydrocarbons or salt mixtures and exposed to magnetic fields up to 64 mT. The mixtures were visually observed for solvent boiling (1-octadecane (315° C.@38 mT)/n-tetracosane (391° C.@59 mT)) or salts melting (ZnCl/NaCl (420° C.@64 mT)). As a secondary confirmation, a $Fe_3O_4$/$YVO_4$:$Eu^{3+}$ mixture (3:1 by wt) was used to estimate the temperature based on the photoluminescent intensity. The $Eu^{3+}$ intensity is known to be inversely proportional temperature. The PL measurements increased linearly above 25 mT (FIG. 2 and Tables 2 and 3), and reached an estimated surface temperature of ~420° C. at 64 mT, comparable to those required for polymer pyrolysis/degradation.

TABLE 2

| PL temperature calibration under $N_2$ gas. | |
| --- | --- |
| Temperature (° C.) | Normalized PL (a.u.) |
| 25 | 1.000 |
| 50 | 0.937 |
| 75 | 0.897 |
| 100 | 0.847 |
| 125 | 0.800 |
| 150 | 0.738 |
| 175 | 0.672 |
| 200 | 0.603 |
| 225 | 0.540 |
| 250 | 0.459 |
| 275 | 0.388 |
| 300 | 0.332 |
| 325 | 0.273 |
| 350 | 0.238 |
| 375 | 0.204 |
| 400 | 0.183 |
| 425 | 0.164 |

TABLE 3

| RF temperature response based on normalized PL intensity. | | |
| --- | --- | --- |
| Field Strength (mT) | Normalized PL (a.u.) | Temperature (° C.) |
| 0 | 1.00 | 23.3 |
| 5.4 | 0.98 | 32.6 |
| 10.8 | 0.96 | 43.2 |
| 16.2 | 0.92 | 62.3 |

TABLE 3-continued

| Field Strength (mT) | Normalized PL (a.u.) | Temperature (° C.) |
|---|---|---|
| 21.6 | 0.80 | 122 |
| 27 | 0.52 | 261 |
| 32.4 | 0.47 | 285 |
| 37.8 | 0.43 | 306 |
| 43.2 | 0.36 | 340 |
| 48.6 | 0.35 | 346 |
| 54 | 0.29 | 375 |
| 59.4 | 0.24 | 399 |
| 64.8 | 0.20 | 420 |

RF temperature response based on normalized PL intensity.

Two types of catalysts were chosen for induction heating based on the TGA screening results, modified ZSM-5 (Ni-ZSM-5, Ni2-ZSM-5, Pt—K-MFI) and $CeO_2$-based catalysts. Commercial $Fe_3O_4$ powder was added to the reactor to act as a magnetic susceptor. Conversions to liquid and gas products are reported in Tables 4 and 5 and the product distributions are reported on a carbon % basis in FIG. 3. Some $H_2$ was also observed (Table 4, as a percentage of the conversion to gas). The gas product RGA and liquid GC-MS scans are shown in FIGS. 7A-7B and 8A-8B. The RGA scans suggest $CH_4$ formation is minimal (FIGS. 7A-7B). Similar results for conventional thermally-driven reactions using the $Ni_2$-ZSM-5 catalyst are also given in Table 4 with the selectivities reported in FIGS. 9A-9B. Comparing the RF and thermal results at similar surface temperature (420° C.), the observed first-order rate constant is 25 times faster for the RF-activated reaction. If the comparison were made on a bulk (fluid) temperature basis, the comparison would be even more in favor of RF activation. Relatively less $H_2$ is also produced under RF conditions (Table 4).

TABLE 4

LDPE conversions for different catalysts with varying applied fields

| Catalyst | Amps | Conversion to gas and liquid Products, % | % Aromatics Carbon Basis | Conversion to coke, % | Mol % $H^2$/ Gas conversion |
|---|---|---|---|---|---|
| Fe—Ni-ZSM-5 | 32 | ~0 | N/A | N/A | N/A |
| | 43 | ~0 | N/A | N/A | N/A |
| | 64 | 77 | 0.81 | 2.0 | 0.21 |
| Fe—Ni2-ZSM-5 | 64 | 58 | 3.7 | 2.0 | 2.1 |
| [1] Fe—Ni2-ZSM-5 | 0 (350° C) | 1.1 | 0 | 2.5 | 6.4 |
| [1] Fe—Ni2-ZSM-5 | 0 (450° C) | 6.5 | 4.0 | 3.2 | 19.0 |
| Fe—Pt—K-MFI | 64 | 82 | 0.43 | 0.33 | 0.02 |
| Fe—Ce—CS—Ni | 64 | 38 | 4.2 | 0.56 | 1.2 |
| (repeat) | 64 | 43 | 4.8 | N/A | N/A |
| Fe—Ni—Ce—Zr | 32 | ~0 | N/A | N/A | N/A |
| | 64 | 51 | 5.1 | 1.1 | 18 |
| Fe—Ni20-CZA40 | 64 | 62 | 1.9 | 5.2 | 33 |
| Fe—Ni | 64 | 49 | 0.0 | 7.1 | N/A |
| Fe | 64 | 45 | 1.2 | 3.2 | 1.4 |

[1] Conventional heating

TABLE 5

LDPE depolymerization using a 64 mT induction field for 2 h under 1 atm $N_2$. Liquid, gas, and coke conversions are on a weight basis with aromatics (one and two ring) selectivity reported on a carbon % basis. Heavier than two-ring aromatics have been identified with "coke."

| Catalyst | Liquid Conversion (wt %) | Gas Conversion (wt %) | Coke Conversion (wt %) | Aromatics[1] (Carbon %) |
|---|---|---|---|---|
| Fe—Ni-ZSM-5 | 2 | 75 | 2.1 | 0.81 |
| Fe—Ni2-ZSM-5 | 4 | 54 | 2.0 | 3.7 |
| Fe—Pt—K-MFI | 2 | 80 | 0.33 | 0.43 |
| Fe—Ce—CS—Ni | 24 | 16 | 0.56 | 4.5 |
| Fe—Ni—Ce—Zr | 26 | 26 | 1.1 | 5.1 |
| Fe—Ni20-CZA40 | 43 | 19 | 5.2 | 1.9 |
| Fe—Ni | 35 | 15 | 7.1 | 0.0 |
| Fe | 26 | 19 | 3.2 | 1.2 |

[1]Single and two-ring. Heavier aromatics have been identified with "coke."

From the fractional amounts (y) of the high temperature peaks in the TPOs, the coke conversions in Tables 4 and 5 could be determined as follows:

$$\% \text{ coke conversion} = \frac{y[W_c + (1-x)W_p]}{W_p} \qquad \text{Eq. 4}$$

Where x is the conversion to gas and liquid products, $W_c$ the weight of catalyst, and $W_P$ the initial polymer weight.

The rate constant for use in Eq. 6 was determined from the conversion data in Table 5 for the Fe—Pt—K-MFI catalyst. For a 1st order reaction:

$$-\ln(1-f) = \frac{k\,C_0}{N_o}V_c\,t = k\,\varepsilon_c\,t \qquad \text{Eq. 5}$$

Where f is fractional conversion, Co the initial concentration of polymer, $N_0$ the initial mols polymer, $V_c$ is the catalyst volume, and $\varepsilon_c$ the catalyst/polymer volume ratio. The rate constant has units [fluid vol/(cat vol×time)], or $s^{-1}$.

The zeolite-based catalysts produced significantly more light gases and light liquids, with the metal oxides generating more diesel-range products. The Ni2-ZSM-5 catalyst generated mostly C2-C3 light gases compared to the Ni-ZSM-5 and Pt—K-MFI, which produced a lot of C4-C5. For Pt—K-MFI, these light gases/liquids are primarily olefins based on preliminary GC-MS analysis (FIGS. 8A-8B). The Ce-based catalysts tended to generate lower molecular weight liquids than Fe or Fe—Ni. As a comparison, the Fe and Fe—Ni samples were run at higher Fe:polymer ratios (1:5 Fe:LDPE) which mimic the catalyst:LDPE ratios used in the other experiments (FIGS. 10A-10B) but would give higher temperatures since there is more $Fe_3O_4$. The product distributions in this case shift to higher concentrations of light gases, suggesting that the cleavage process generates lower molecular weight hydrocarbons at higher temperatures. While there was no effort to exactly quantify the relative amounts of alkenes/alkanes, the liquid products are roughly in the 1:1-2:1 range. Similar to the TGA/DSC results, Ni on the commercial $Al_2O_3$—$CeO_2$—$ZrO_2$ support gave a higher total conversion (by 10%).

Catalyst Characterization

Figure 4A:
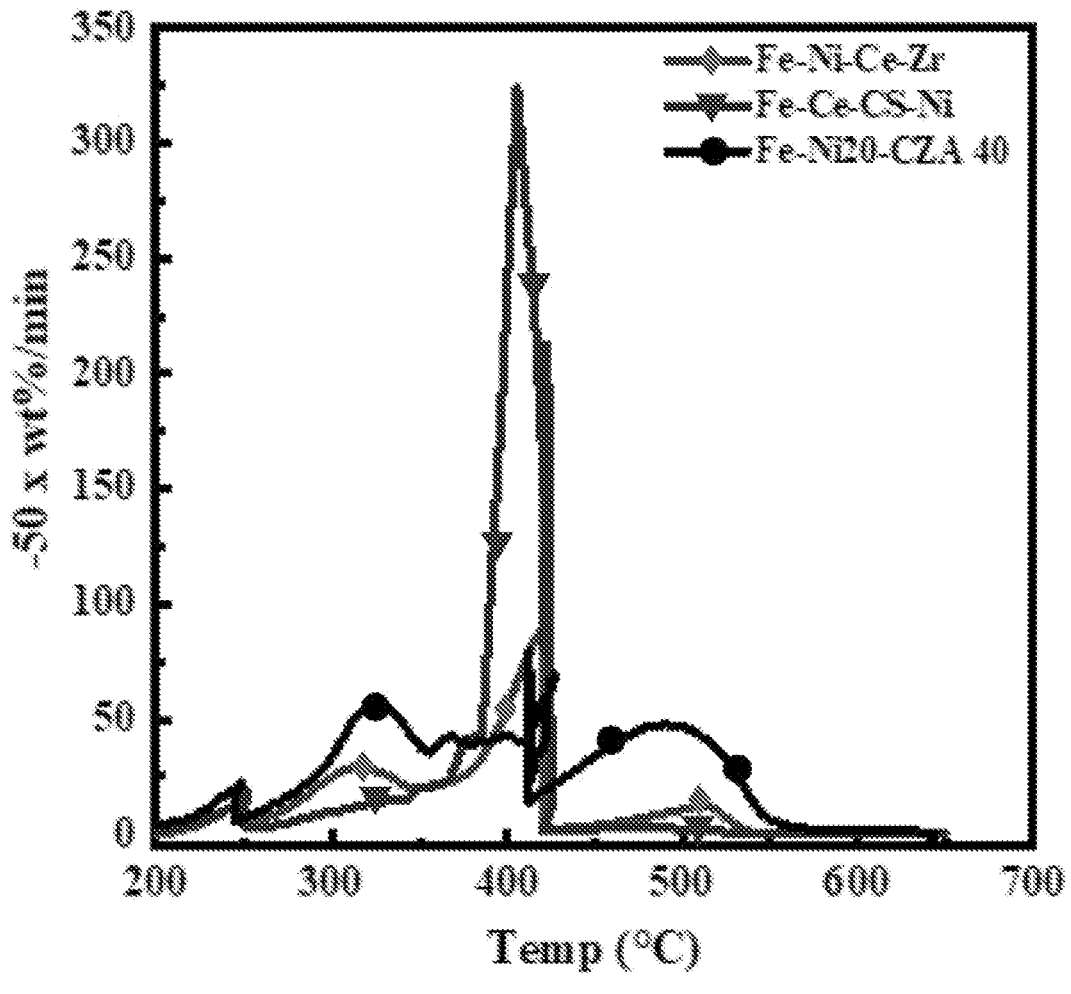
Figure 4B:
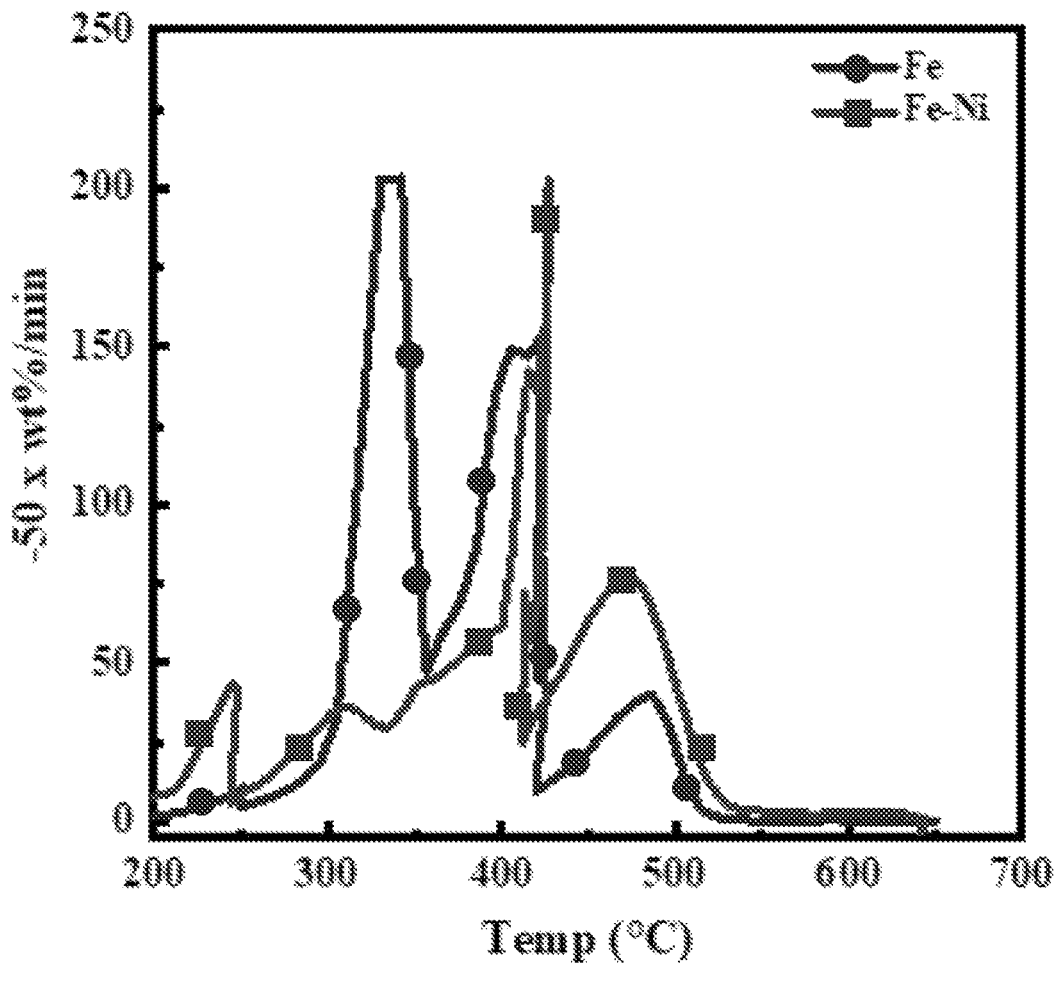
Figure 4C:
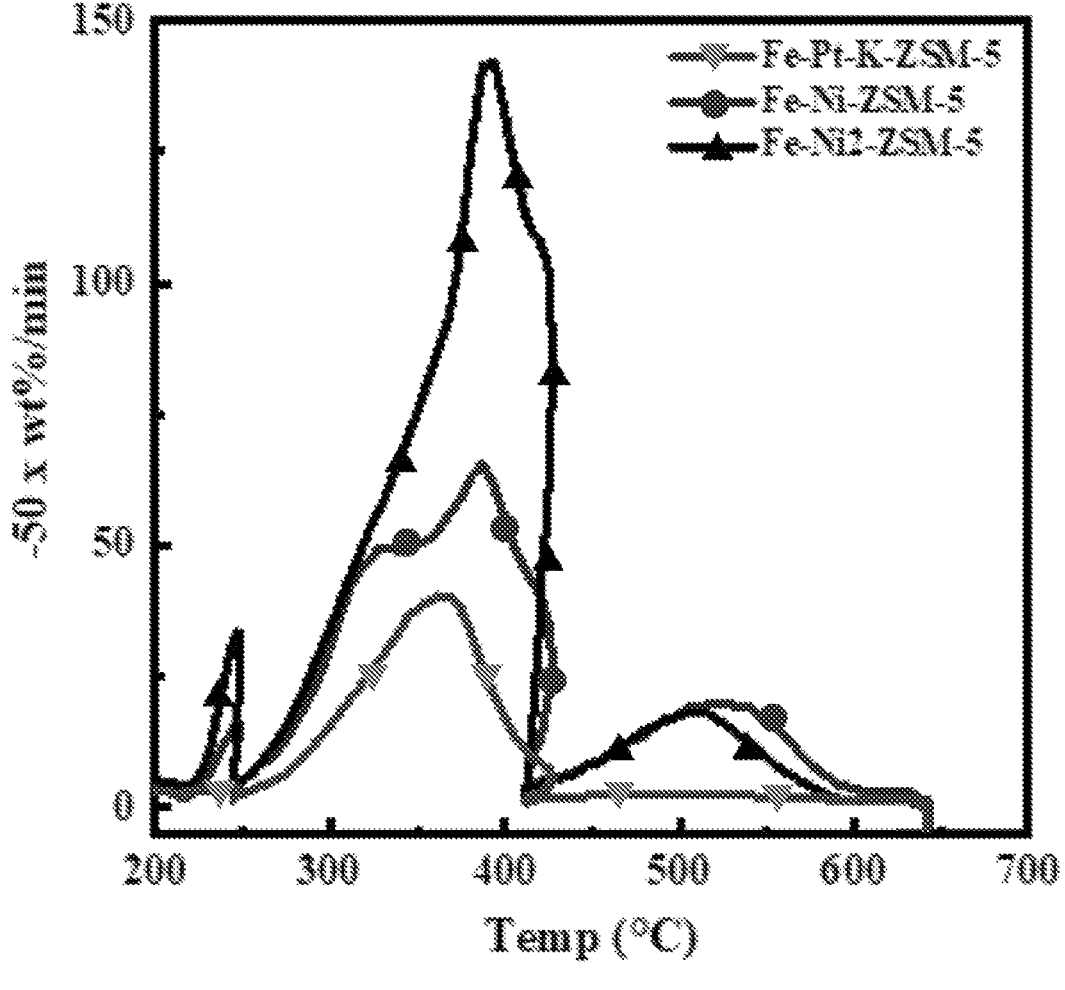

The used, extracted catalysts were analyzed by TPO to estimate how much of the polymer was converted to heavier aromatic or graphitic ("coke") material (FIGS. 4A-4C). The coke conversions were calculated using eq. 4 and reported in Table 5. There was a small peak at <200° C. (not shown) due to solvent vaporization. The peaks between 220-420° C. are attributed to the oxidation of the residual polymer with the higher temperature peaks (>420° C.) arising from coke/heavy aromatics oxidation. This was checked by running both LDPE and HDPE standards where unreacted polymer and catalyst were ground together. Additionally, the $Fe_3O_4$ is oxidized to $Fe_2O_3$ during the oxidation process between 400-600° C. However, the contribution to the weight changes caused by this oxidation is negligible, calculated as only 0.1% maximum. As a secondary confirmation of the presence of some heavy carbon products, Raman spectroscopy was performed on a select set of used samples to identify the presence of a small graphitic GO band (1595-1605 $cm^{-1}$).

Figure 4D:
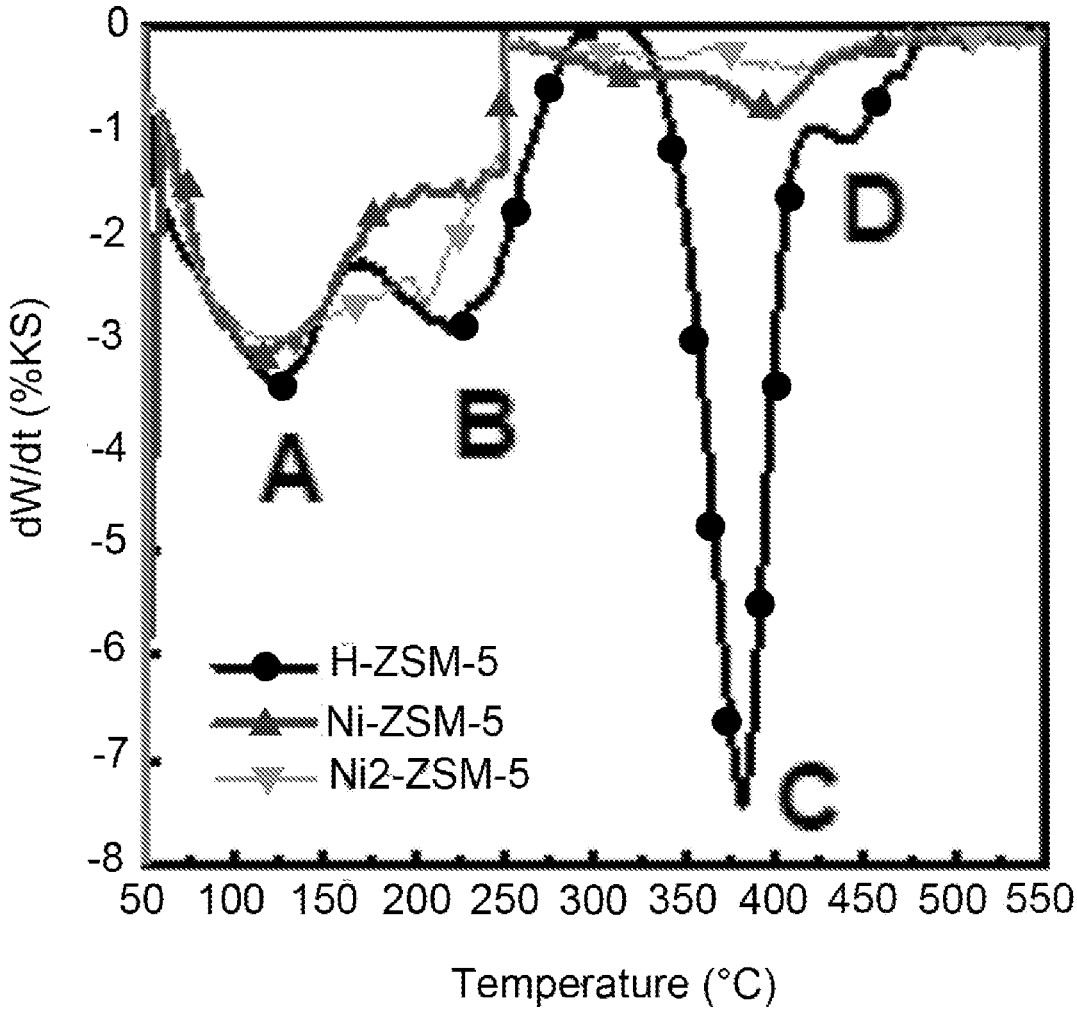

Finally, to understand the nature of the surface sites within the ZSM-5 catalysts, the Brønsted/Lewis acid site concentrations and strengths were quantified. The split between Brønsted, weak Lewis and strong Lewis acid sites in the zeolites was assessed using a 1-propanamine (1-PA) desorption method pioneered by Gorte and modified for metal-exchanged materials by Price and Dooley. The 1-PA accurately titrates Brønsted sites in H-form zeolites, and can provide reasonable estimates of residual Brønsted sites in metal-exchanged zeolites, because desorption peaks associated with 1-PA on the ionic metals shift to higher or lower temperatures. This titration also detects framework atoms that might give rise to weaker acid sites, and their departure from the framework. An example analysis for the three ZSM-5-based catalysts is shown (FIG. 4D). The low temperature peaks (peaks A and B) are associated with weak Lewis acid interactions with the 1-PA. The 1-PA associated with $H^+$ in the zeolite framework desorbs at 350-410° C. (peak C). Replacing these with $Ni^{2+}$ results in a sharp decrease of this peak, essentially disappearing for the overloaded Ni2-ZSM-5. Unlike the case for certain exchanged metals ($Ga^+$ or $Al^{3+}$), there is no evidence for the generation of strong Lewis sites by $Ni^{2+}$ (peak D in FIG. 4D). The total amounts of 1-PA adsorbed decrease even at the lower temperatures (peak B), suggesting weaker Lewis acidity associated with these metal-exchanged (or in the case of Ni2-ZSM-5, exchanged Ni but also additional NiO). However, the coordination of the active Ni is not the same as in NiO, because the Ni-SBA catalyst, with Ni impregnated into high surface area SBA-16, showed no activity. This suggests that some degree of Ni-zeolite coordination at framework sites is necessary for a functioning depolymerization catalyst of this type, as also seen with the poorer activity of the reduced Ni(0)-ZSM-5.

Discussion

Mostly Ni-based catalysts were chosen for depolymerization under the hypothesis that catalysts which can oligomerize low molecular weight olefins should also catalyze the reverse reaction. The only problem with the catalysts containing Ni impregnated into $CeO_2$ is their lower activity. The $CeO_2$-based catalyst with a high wt % Ni (Ni20-CZA40) gave more coke than the zeolite-based catalysts, but, as expected, the $CeO_2$-based catalysts with only a few wt % Ni gave very little coke. The cleavage mechanism of the Ce-based metal oxides produced diesel-range hydrocarbons of a fairly narrow molecular weight distribution with minimal light gases, giving these catalysts an advantage over the zeolites if diesel is desired. However, the two experiments with $Ni/Fe_3O_4$(Fe—Ni) showed that it is also possible to control the product distribution based on applied heat (higher surface temperature), even with a simpler catalyst.

It was hypothesized that the differences in product distributions for the zeolites compared to the metal oxides result from cleavage nearer to terminal carbon groups within the zeolite pores. This is not an artifact of higher conversion. Note that the product distribution for the Ni20-CZA40 is still skewed toward heavier liquid products, while its activity is comparable to the Ni-zeolite catalysts. Lopez et al. postulated that for zeolite-based catalysts the depolymerization reaction generally occurs on the zeolite crystal surfaces rather than within the pores, due to diffusion limitations. However, this is somewhat contrary to previous literature regarding pore diffusion of long chain molecules in zeolites, and in mesoporous $SiO_2$. Can polyethylene chains enter the zeolite pores? A cutoff minimum effective diffusivity ($D_e$) was determined of $3\times10^{-15}$ $m^2/s$ for spherical particles (dp=2 µm) of the type used here:

$$(D_e) = \frac{k}{\varepsilon_c \, \phi^2} \left(\frac{d_p}{6}\right)^2 \qquad \text{Eq. 6}$$

assuming a Thiele modulus ($<$p) of 1, a rate constant $k=2.4\times10^{-3}$ s$^{-1}$ (calculated as shown in Eq. 5), and a catalyst/polymer ratio ($E_c$) of 0.1. The bulk diffusivity for polyethylene (in the melt, over a wide range of molecular weights, branching levels, and grades) at 200° C. is between $2\times10^{-14}$-$3\times10^{-12}$ m$^2$/s. In its random coil state, no polymer molecule could penetrate a microporous material such as a zeolite. The radius of gyration for PE (similar to its hydrodynamic radius RH) is still $>4$ nm at 150° C., and ratios of $R_{H, \; polymer}/R_{pore}>\sim0.2$-0.4 are known to reduce $D_e$'s to effectively zero. But the strong heats of adsorption in the zeolites (they increase linearly with carbon number for most zeolites and silicas), and the gains in conformational entropy upon "flattening" the chains to a more planar zig-zag configuration, drive the diffusive process at high temperatures in microporous materials, absent specific repulsive interactions. For zeolites, the intraparticle diffusivities of the alkane/alkene families approach a constant minimum ($>10^{-11}$ m$^2$/s) with respect to molecular weight even at short chain lengths, at temperatures much lower than used here. Recent solid-state NMR measurements for HDPE in meso-SiO$_2$ (1.5 nm pores) suggest even higher diffusivities, $\sim2\times10^{-9}$ m$^2$/s at 114° C. This type of conformational change for alkyl chains is well-known in catalysis; for example, for triglyceride hydrogenation measured $D_e$'s can actually be 2-6 times greater than bulk diffusivities (due to surface diffusion of planar zig-zag conformers), and in size-exclusion chromatography polyolefins routinely penetrate pores far smaller than their presumed hydrodynamic radii. It is concluded that for the rates observed here, the reactions are not diffusion-limited and that the polymer chains can penetrate the pores of ZSM-5 to some extent.

We expect differences in reactivity for purely ion-exchanged vs. extra-framework Ni even using the same zeolite (ZSM-5), as observed above (Table 5, FIG. 3). Specifically, the Ni$^{2+}$ (or slightly less electropositive) coordination within the zeolite dictates electron back donation to the antibonding states, affecting the available d-band states for polymer interaction. The Ni$^{2+}$-exchanged zeolites (at least in the AFI and LTA topologies) are known to drive polymerization by converting to immobilized alkyl complexes apparently capable of both β-hydride elimination and olefin insertion in a likely Cossee-Arlman-type mechanism. DFT calculations have shown that such immobilized Ni$^{2+}$ mimics homogenous catalysts, in some cases achieving a preferred (for polymerization) square-planar coordination. The zeolite structure also promotes chain growth via diffusion-limited processes. Therefore, highly dispersed (via Si—O—Al exchange sites) and immobilized Ni$^{2+}$ (and Pt$^+$) sites within the zeolite should be able to reversibly depolymerize by a reverse Cossee-Arlman mechanism. All of these M-exchanged zeolites give high selectivities to lighter carbon products, as might be expected from such a mechanism. However, the Ni-ZSM-5 shows residual strong acid sites (Brønsted acid) by 1-PA titration, which could account for the lower ethylene selectivity.

In contrast, the Ni$^{2+}$-doped rare earth oxides and Ni/Fe$_3$O$_4$ must catalyze depolymerization by an entirely different mechanism. It has been found that for other supported organometallic complexes such as Zr oxyhydrides/SiO$_2$ that scission is almost random in nature at 150° C. Some product selectivity is occurring with these samples, because there were essentially no products observed above C20 for the Ni—CeO$_2$ based catalysts. Extended extraction times and extractions with a slightly better solvent for HDPE (o-xylene) also gave no higher weight products. On the other hand, the Fe and Fe—Ni did generate higher weight products, suggesting a more random cleavage process. Therefore, the Ni—CeO$_2$ product distributions, centered around C7-C14, reflect intrinsic depolymerization activity of these catalysts, instead of purely random scission. Whether this arises from a diffusional cutoff related to pore size and/or certain preferred conformations of $>$C20 species in larger pores is an open question.

We can compare the disclosed process to that of a typical microwave-initiated depolymerization for HDPE. In this process, the 1:1 FeAlOx/HDPE catalyst mixture generated temperatures starting at 350 extending to $>$400° C. during a run. For the first cycle, they obtained gas yields of $\sim$65% (mass basis), with most of the remaining product detected as coke or iron carbide. The gas was composed of 80 vol % H$_2$ and 5-10% CO with the remainder consisting of CH$_4$, CO$_2$ and C$^{2+}$ gases. The different mechanisms seen between the microwave process and the disclosed RF-activated depolymerization can be attributed to differences in how microwave vs. RF radiation interacts with the polymer and catalyst. In the RF-driven process, there is localized hysteresis heating of the Fe$_3$O$_4$ followed by the activation of C—C bonds within the hydrocarbon backbone instead of direct activation of the hydrocarbons.

Finally, depolymerizations of commercial LDPE (grocery bags), commercial polystyrene (Styrofoam), and virgin HDPE were performed over the Fe—Ni catalyst as proof-of-concept experiments. For commercial LDPE, the depolymerization conversion after 2 h for a 115:1000 cat: polymer wt ratio was 54% (28.4% liquid, 19.4% gas, 6.5% coke) with product selectivities shown in FIG. 5. This conversion and the selectivities are similar to the virgin polymer. The conversion for the commercial polystyrene was 33% and that of the virgin HDPE 48%. The HDPE depolymerization has a similar selectivity as the LDPE, with the products centered around C13-C14, but generated more light liquid products. The process appears to work for all common polyolefins.

Example 3: Polymer Depolymerization with Platinum (Pt)-Loaded Zeolite Catalysts Catalyst Synthesis The zeolites (MFI, LTL or just L, TON and SSZ-13 structure types) were ion-exchanged to the K$^+$ form twice with excess 0.1 M KOH at 80° C. (or with a mixture of KOH and 0.1 M Ba(NO$_3$) for Ba—K-L), dried at 120° C. overnight, then at 350° C. in flowing air. The Pt was added to the K$^+$-exchanged zeolites (Pt/K-TON, Pt/K-SSZ-13, Pt/K-MFI, Pt/Ba—K-L) by contacting overnight with dilute aqueous platinum diaminodinitrite at pH=10. The solution was evaporated at 120° C., dried overnight, then reduced with 5% H$_2$ at 500° C. for 6 h. For the Pt—Sn (platinum-tin) catalysts, the desired amount of tetrabutyltin was dissolved in pentane and the zeolite impregnated under N$_2$, dried under N$_2$ at 120° C. for 3 h, and then impregnated with Pt in the same way as the Pt-only catalysts. These Pt—Sn catalysts were calcined in 30% O$_2$/Ar, at 300° C. for 3 h, then reduced with H$_2$ at 400° C.

Surface areas and pore volumes were determined by N$_2$ porosimetry. The Pt dispersions (estimated %'s of accessible Pt atoms at 23° C.) were determined by pulse chemisorption of H$_2$ assuming one atom H/surface Pt. The ion-exchanged $H^+$ sites were titrated by 1-propanamine adsorption/desorption. For the $H^+$-form zeolites, this experiment gives the framework Si/Al molar ratio. The final reduced catalysts showed no measurable ion-exchanged $H^+$ sites (i.e., those which would desorb 1-propanamine at >350° C.). These properties of the catalysts are shown in Table 6.

change upon drying a sample of catalyst/product mass under vacuum at 190° C. for 4 d. Coke amounts were determined by temperature-programmed oxidation (TPO) in air. The combined gas, liquid, and coke analyses along with the conversions were combined to determine mol % of all

TABLE 6

Properties of Pt-Loaded Zeolite Catalysts Used for Depolymerization of LDPE

| Catalyst | Si/Al | Pt loading (wt %) | Sn loading (wt %) | Surface Area ($m^2/g$) | Pore Volume, $cm^3/g$ | Pt Dispersion (%) |
|---|---|---|---|---|---|---|
| Pt/K-MFI | 20 | 0.5 | — | 370 | 0.25 | 34 |
| PtSn/K-MFI | 20 | 0.5 | 0.7 | 300 | 0.18 | 65 |
| Pt/Ba-K-L | 9 | 0.8 | — | 190 | 0.2 | 92 |
| PtSn/K-L | 9 | 1 | 1 | 180 | 0.19 | 30 |
| Pt/K-TON | 55 | 0.8 | — | 53 | 0.11 | 31 |
| Pt/K-SSZ-13 | 16 | 0.8 | — | 250 | 0.27 | 13 |
| [1]Sn/K-MFI | 20 | — | 7.3 | N/A | N/A | — |
| [1]Fe$_3$O$_4$ | — | — | — | 33 | 0.11 | — |

[1]Did not adsorb $H_2$ at 23° C.

RF-Activation Reaction Experiments 200 mg of the catalyst/Fe$_3$O$_4$ powder (1:1 wt ratio) was mixed with 1 g LDPE polymer (924 kg/m$^3$ density, melting point 105-115° C.). The mixture was loaded into a glass reactor, purged with N$_2$, and exposed to the RF field (200-600 A, 22-64 mT) for 2 h. A 500 A RF energy input (54 mT) gives roughly a 375° C. surface temperature, and the corresponding temperatures for other currents are: 400 A, 340° C.; 300 A, 285° C.; 200 A, 122° C.

The gas atmosphere was sampled and analyzed by injection into a residual gas analyzer operating in selective ion mode. Other (liquid) depolymerization products were extracted from the remaining polymer/catalyst mixture with products on a combined basis. The product selectivity (Si) is then defined as (C$_i$ is the number of carbons in the compound):

$$(S_i) = \frac{(100)(\text{mol } \%_i)(C_i)}{\sum (\text{mol } \%_i)(C_i)} \qquad \text{Eq. 7}$$

The results of depolymerization experiments using commercial LOPE are shown in Table 7.

TABLE 7

Depolymerization of LDPE with Pt-Loaded Zeolite Catalysts[1]

| Catalyst | Surface Temperature (° C.) | Gas X (wt %) | Liquid X (wt %) | Coke X (wt %) | Total X (wt %) |
|---|---|---|---|---|---|
| 0.8% Pt/Ba—K-L | 375 | 28.5 | 33.7 | 0.4 | 62.6 |
| 1% Pt-1% Sn/K-L | 375 | 30.5 | 63.5 | 0.1 | 94.1 |
| 1% Pt-1% Sn/K-L | 340 | 21.1 | 54.1 | 0.2 | 75.4 |
| 1% Pt-1% Sn/K-L | 285 | 8.1 | 20.9 | 3.4 | 32.4 |
| 1% Pt-1% Sn/K-L | 122 | 6.3 | 19.4 | 2.1 | 27.8 |
| 0.5% Pt/K-MFI | 420 | 80.9 | 1.5 | 0.3 | 82.7 |
| 0.5% Pt/K-MFI | 375 | 54.8 | 4.3 | 1.3 | 60.4 |
| 0.5% Pt/K-MFI | 340 | 50.5 | 4.8 | | 55.3 |
| 0.5% Pt/K-MFI | 285 | 35.6 | 4.0 | | 39.6 |
| 0.5% Pt/K-MFI | 122 | 1.9 | 0.3 | | 2.2 |
| 0.6% Pt-0.7% Sn/K-MFI | 375 | 27.5 | 43.8 | 0.7 | 72.0 |
| 0.6% Pt-0.7% Sn/K-MFI | 340 | 26.6 | 37.0 | | 63.5 |
| 0.6% Pt-0.7% Sn/K-MFI | 285 | 14.6 | 28.4 | | 42.9 |
| 0.6% Pt-0.7% Sn/K-MFI | 122 | 0.7 | 0.5 | | 1.2 |
| 0.8% Pt/K-TON | 375 | 48.9 | 16.8 | 2.0 | 67.7 |
| 0.8% Pt/K-SSZ-13 | 375 | 38.9 | 56.2 | 0.2 | 95.3 |
| Fe$_3$O$_4$ | 375 | 12.8 | 27.4 | — | 40.2 |
| Fe$_3$O$_4$ | 340 | 7.3 | 19.4 | — | 26.7 |
| Fe$_3$O$_4$ | 285 | 5.5 | 12.7 | — | 18.2 |
| Fe$_3$O$_4$ | 122 | 0.3 | 0.5 | — | 0.8 |

[1]X = % conversion from polymer.

dichloromethane for 5 d. The liquid products were then analyzed by GC-MS. The conversion to gases was determined from the weight change before and after reaction. The conversion to liquids was determined from the weight The results show that reasonable conversions of the LOPE to light gases and liquids are possible with Pt-loaded zeolites even at surface temperatures as low as 285° C., with much higher conversions possible at 340 and 375° C. PtSn/K-L and Pt/K-SSZ-13 are the most active catalysts (ca. 95 wt % total conversion) for the RF depolymerization of LOPE at 375° C. for 2 h. PtSn/K-L is also best at making liquid products at 375° C., coupled with the lowest production of coke. When Pt was supported on the L zeolite without any Sn, the liquid yield dropped by half with no significant change in gas yield, but a slight increase in coke formation. Comparing results from Pt-containing L, TON, SSZ-13, and MFI zeolites, it is evident that the dispersion of the Pt plays little to no role in the overall activity, while the morphology of the zeolite and the presence of Sn does. Catalysts with Pt on MFI and TON, both of which are known to have smaller pore sizes, 0.51-0.57 nm and 0.46-0.57 nm respectively, were selective to lighter products (FIG. 11A). But Pt/K-SSZ-13 was not. While it is does have small intracrystalline pores (8, 6 and 4 ring pore openings), it also contains larger ~7.37 A diameter supercages, and, as seen in Table 6, a high surface area and pore volume.

Overall, Pt/K-MFI generated the highest alkene to alkane ratio, due to its formation of mostly light products (FIG. 11B), so more cracking events took place. Even though different catalysts generated different ratios of alkenes to alkanes, there is a similar trend of decreasing alkene/alkane ratio with respect to increasing carbon number for the liquid products (>C5). Therefore, the type of catalyst and process conditions can be optimized to maximize the production of either alkenes or alkanes, at the expense of a reduction in average molecular weight. This behavior is consistent with the lack of significant aromatics or coke production.

From Table 7, it is seen that the total conversion is reduced by 15-30% between 400 and 300 A, or roughly 340 to 285° C. surface temperature. For thermal depolymerization essentially no activity was found for the zeolite catalysts until ~350° C., and even then the conversions were low. The RF induction heating-driven process is more effective in heat transfer to the catalyst, with some activity even taking place at temperatures near the LDPE melting point.

It is also true that the $Fe_3O_4$ itself catalyzes some depolymerization as shown in Table 1. However, the activity is relatively low, with almost no activity at 200 A (122° C.). Notably, the product distributions for the Pt-only catalysts look very different from product distributions for $Fe_3O_4$ alone, which are skewed more toward higher molecular weight products. The distributions for PtSn catalysts are also skewed toward higher molecular weight alkenes/alkanes, but at much higher polymer conversions. This proves that when a zeolite is mixed with $Fe_3O_4$, it is the zeolite doing most of the catalysis, even though the $Fe_3O_4$ by itself is somewhat active.

Example 4: Conclusions

In summary, LDPE and HDPE depolymerization was studied using thermal and induction heating of Ni-activated zeolites, metal oxides, and Pt-activated zeolites, without added $H_2$. The thermal decomposition process agreed well with previous results showing the onset of polymer decomposition around 350° C., regardless of the catalyst structure, but requiring significantly long reaction times for high conversion. Alternatively, the RF-driven process resulted in high conversions (up to 95%) after exposure to 54-64 mT fields for 2 h. The surface temperatures were calibrated using the m.p./b.p. of different solvent. The depolymerization process was shown to be dependent upon catalyst structure. The inclusion of Pt in a wide range of small- and medium-pore size zeolites results in catalysts that show moderate to high depolymerization activity down to surface temperatures as low as 285° C. The addition of Sn to these Pt-loaded zeolites further enhances catalyst activity and shifts the selectivity more to higher value liquid products of carbon number $C_8$ and greater.

Finally, the depolymerization of commercial LDPE (grocery bags) over a Fe—Ni catalyst produced mainly $C_{10}$-$C_{20}$ alkanes/alkenes. The novelty of this work is that the RF-driven depolymerization process allows for controlled (minimal $CH_4$ and $H_2$) and product-tunable decomposition of virgin and commercial grade polyolefins to rapidly (at least 25 times faster than the corresponding thermally-driven reaction) produce either light gases or diesel-grade products with no added $H_2$. Little coke is produced, even at high conversions. The process has the potential to upcycle a range of commercial plastics into monomers or specialty chemical feedstocks without employing either noble metals or $H_2$ feeds as an economically viable alternative to current recycling methods.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Abu-Laban, M.; et al, Ex-situ up-conversion of biomass pyrolysis bio-oil vapors using Pt/Al2O3 nanostructured catalyst synergistically heated with steel balls via induction. Catalysis Today 2017, 291, 3-12.
2. Achilias, D. S.; et al, Glycolytic depolymerization of PET waste in a microwave reactor. Journal of Applied Polymer Science 2010, 118 (5), 3066-3073.
3. Bachus, R.; et al, Molecular weight and temperature dependence of self-diffusion coefficients in polyethylene and polystyrene melts investigated using a modified n.m.r. field-gradient technique. Polymer 1983, 24, 964-970.
4. Bishop, M. T.; et al, Dynamic Light-Scattering Studies of Polymer Diffusion in Porous Materials: Linear Polystyrene in Porous Glass. Macromolecules 1989, 22, 1220-1231.
5. Blyholder, G., Molecular Orbital View of Chemisorbed Carbon Monoxide. The Journal of Physical Chemistry 1964, 68 (10), 2772-2777.
6. Brandrup, J.; et al, Polymer Handbook, 4th Ed. John Wiley: New York, 1999; Vol. II/365.
7. Brites, C. D. S.; et al, Lanthanide-Based Thermometers: At the Cutting-Edge of Luminescence Thermometry. Advanced Optical Materials 2019, 7 (5), 1801239.
8. Brogaard, R. Y.; et al., Ethene Dimerization on Zeolite-Hosted Ni Ions: Reversible Mobilization of the Active Site. ACS Catalysis 2019, 9 (6), 5645-5650.
9. Brogaard, R. Y.; et al, Ethene Oligomerization in Ni-Containing Zeolites: Theoretical Discrimination of Reaction Mechanisms. ACS Catal. 2016, 6, 1205-1214.
10. Celik, G.; et al, Upcycling Single-Use Polyethylene into High-Quality Liquid Products. ACS Central Science 2019, 5 (11), 1795-1803.
11. Chandrasekaran, S. R.; et al, Catalytic Thermal Cracking of Postconsumer Waste Plastics to Fuels. 1. Kinetics and Optimization. Energy & Fuels 2015, 29 (9), 6068-6077.

12. Closed Loop Partners, Advancing Circular Systems for Plastics; https://www.closedlooppartners.com/research/advancing-circular-systems-for-plastics/ (accessed July 2020).

13. De Stefanis, A.; et al, Catalytic pyrolysis of polyethylene: A comparison between pillared and restructured clays. Journal of Analytical and Applied Pyrolysis 2013, 104, 479-484.

14. Dufaud, V. et al., Catalytic Hydrogenolysis at Low Temperature and Pressure of Polyethylene and Polypropylene to Diesels or Lower Alkanes by a Zirconium Hydride Supported on Silica-Alumina: A Step Toward Polyolefin Degradation by the Microscopic Reverse of Ziegler-Natta Polymerization. Angewandte Chemie International Edition 1998, 37 (6), 806-810.

15. Ehrmaier, A.; et al, Dimerization of Linear Butenes on Zeolite-Supported Ni2+. ACS Catalysis 2019, 9 (1), 315-324.

16. Fleischer, G., The chain length dependence of self-diffusion in melts of polyethylene and polystyrene. Colloid and Polymer Sci. 1987, 265, 89-95.

17. Garcia-Aguilar, J.; et al, Magnetic zeolites: novel nanoreactors through radiofrequency heating. Chemical Communications 2017, 53 (30), 4262-4265.

18. Geyer, R.; et al, Production, use, and fate of all plastics ever made. Sci. Adv. 2017, 3, e1700782-1-5.

19. Gorte, R. J., What do we know about the acidity of solid acids? Catal. Lett. 1999, 62, 1-13.

20. Hammer, B.; et al, Why gold is the noblest of all the metals. Nature 1995, 376 (6537), 238.

21. Jiang, C.; et al, Rapid screening of ternary rare-earth—Transition metal catalysts for dry reforming of methane and characterization of final structures. Journal of Catalysis 2019, 377, 332-342.

22. Jiang, X.; et al, Trisodium citrate-assisted synthesis of highly water-dispersible and superparamagnetic mesoporous Fe3O4 hollow microspheres via solvothermal process. J. Alloys Comps. 2015, 636, 34-39.

23. Jie, X.; et al, Microwave-initiated catalytic deconstruction of plastic waste into hydrogen and high-value carbons. Nature Catal. 2020, 3, 902-912.

24. Kanazirev, V.; et al, Thermal Analysis of Adsorbed Propanamines for the Characterization of Ga-MFI Zeolites. J. Catal. 1994, 146, 228-236.

25. Kang, M. J.; et al, Depolymerization of PET into terephthalic acid in neutral media catalyzed by the ZSM-5 acidic catalyst. Chemical Engineering Journal 2020, 398, 125655.

26. Karger, J.; et al, Diffusion in Nanoporous Materials: Novel Insights by Combining MAS and PFG NMR. Processes 2018 2018, 6, 147.

27. Kathawalla, I. A.; et al, Hindered Diffusion of Porphyrins and Short-Chain Polystyrene in Small Pores. Macromolecules 1989, 22, 1215-1219.

28. Kofke, T. J. G.; et al, Stoichiometric Adsorption Complexes in [B]- and [Fe]-ZSM-5 Zeolites J. Catal. 1989, 116, 252-262.

29. Kroenlein, K., Thermodynamics Source Database, Thermodynamics Research Center. In NIST Chemistry WebBook, NIST Standard Reference Database Number 69, Linstrom, P. J.; Mallard, W. G., Eds. https://doi.org/10.18434/T4D303 (retrieved Dec. 31, 2020).

30. Kumar, N.; et al, Dimerization of 1-butene in liquid phase reaction: Influence of structure, pore size and acidity of Beta zeolite and MCM-41 mesoporous material. Microporous and mesoporous materials 2012, 147 (1), 127-134.

31. Kunwar, B.; et al, Catalytic and thermal depolymerization of low value post-consumer high density polyethylene plastic. Energy 2016, 111, 884-892.

32. Kunwar, B.; et al, Catalytic Thermal Cracking of Post-consumer Waste Plastics to Fuels. 2. Pilot-Scale Thermochemical Conversion. Energy & Fuels 2017, 31 (3), 2705-2715.

33. Liu, Y.; et al, Pyrolysis of polystyrene waste in a fluidized-bed reactor to obtain styrene monomer and gasoline fraction. Fuel Proc. Technol. 2000, 63 (1), 45-55.

34. López, A.; et al, Deactivation and regeneration of ZSM-5 zeolite in catalytic pyrolysis of plastic wastes. Waste Management 2011, 31 (8), 1852-1858.

35. Marbaix, J.; et al, Tuning the Composition of FeCo Nanoparticle Heating Agents for Magnetically Induced Catalysis. ACS Applied Nano Materials 2020, 3 (4), 3767-3778.

36. Meffre, A.; et al, Complex Nano-objects Displaying Both Magnetic and Catalytic Properties: A Proof of Concept for Magnetically Induced Heterogeneous Catalysis. Nano Letters 2015, 15 (5), 3241-3248.

37. Miandad, R.; et al, Plastic waste to liquid oil through catalytic pyrolysis using natural and synthetic zeolite catalysts. Waste Management 2017, 69, 66-78.

38. Milovanovid, J.; et al, Insights into the Microwave-Assisted Mild Deconstruction of Lignin Feedstocks Using NiO-Containing ZSM-5 Zeolites. ACS Sustainable Chemistry & Engineering 2016, 4 (8), 4305-4313.

39. Nakaji, Y.; et al, Regioselective hydrogenolysis of alga-derived squalane over silica-supported ruthenium-vanadium catalyst. Fuel Processing Technology 2018, 176, 249-257.

40. Oya, S. i.; et al, Catalytic production of branched small alkanes from biohydrocarbons. ChemSusChem 2015, 8 (15), 2472-2475.

41. Pérez-Camacho, M. N.; et al, Biogas reforming using renewable wind energy and induction heating. Catalysis today 2015, 242, 129-138.

42. Price, G. L.; et al, Characterization of [Ga]MFI via thermal analysis. Zeolites 1995, 15, 725-731.

43. Ramirez, E.; et al, Intraparticle Diffusion Mechanisms in SC Sunflower Oil Hydrogenation on Pd. AIChE J 2006, 52, 1539-1553.

44. Ravi, M.; et al, Towards a better understanding of Lewis acidic aluminium in zeolites. Nature Materials 2020, 19 (10), 1047-1056.

45. Rizzarelli, P.; et al, Determination of polyethylene in biodegradable polymer blends and in compostable carrier bags by Py-GC/MS and TGA. Journal of Analytical and Applied Pyrolysis 2016, 117, 72-81.

46. Safavinia, B.; et al, Enhancing Cex Zr1-xO2 Activity for Methane Dry Reforming Using Subsurface Ni Dopants. ACS Catalysis 2020, 10, 4070-4079.

47. Scott, D.; et al, Fast pyrolysis of plastic wastes. Energy & Fuels 1990, 4 (4), 407-411.

48. Shah, J.; et al, Catalytic pyrolysis of LDPE leads to valuable resource recovery and reduction of waste problems. Energy Conversion and Management 2010, 51 (12), 2791-2801.

49. Sharma, B. K.; et al, Production, characterization and fuel properties of alternative diesel fuel from pyrolysis of waste plastic grocery bags. Fuel Processing Technology 2014, 122, 79-90.

50. Siddiqui, M. N.; et al, Hydrolytic depolymerization of PET in a microwave reactor. Macromolecular Materials and Engineering 2010, 295 (6), 575-584.

51. Siemer, M.; et al, Insights into Spectator-Directed Catalysis: CO Adsorption on Amine-Capped Platinum Nanoparticles on Oxide Supports. ACS Applied Materials & Interfaces 2020, 12 (24), 27765-27776.

52. Smit, B. et al, Molecular Simulations of Zeolites: Adsorption, Diffusion, and Shape Selectivity. Chem. Rev. 2008, 108, 4125-4184.

53. Tennakoon, A.; et al, Catalytic upcycling of high-density polyethylene via a processive mechanism. Nature Catal. 2020, 3, 893-901.

54. Vinum, M. G.; et al, Dual-Function Cobalt-Nickel Nanoparticles Tailored for High-Temperature Induction-Heated Steam Methane Reforming. Angewandte Chemie 2018, 130 (33), 10729-10733.

55. Wang, W.; et al, Induction Heating: An Enabling Technology for the Heat Management in Catalytic Processes. ACS Catalysis 2019, 9 (9), 7921-7935.

56. Wei, J.; et al, Controllable Preparation and Catalytic Performance of Magnetic Fe3O4@CeO2Polysulfone Nanocomposites with Core-Shell Structure. Ind. Eng. Chem. Res. 2018, 57, 15039-15045.

57. Weisz, P. B.; et al, Catalytic production of high-grade fuel (gasoline) from biomass compounds by shape-selective catalysis. Science 1979, 206 (4414), 57-58.

58. World Economic Forum. The World's Plastic Problem in Numbers. https://www.weforum.org/agenda/2018/08/the-world-of-plastics-in-numbers (accessed Jul. 12, 2019).

59. Yeh, Y.-H.; et al, Study of Zn and Ga Exchange in H—[Fe]ZSM-5 and H—[B]ZSM-5 Zeolites. Ind. Eng. Chem. Res. 2016, 55, 12795-12805.

60. Zhang, F.; et al, Polyethylene upcycling to long-chain alkylaromatics by tandem hydrogenolysis/aromatization. Science 2020, 370, 437-441.

61. Zhao, R.; et al, Polymer-Polymer Mutual Diffusion via Rheology of Coextruded Multilayers. AIChE J 2007, 53, 978-985.

62. Zhu, L.; et al; in, Polymer Handbook, 4th Ed. John Wiley: New York, 1999; Vol. 5.

63. Zupancic, I.; et al, NMR Self-Diffusion Study of Polyethylene and Paraffin Melts. J. Polym. Sci. Polym. Phys. 1985, 23, 387-404.

What is claimed is:

1. A method for depolymerizing plastic, the method comprising:
(a) providing a plastic material;
(b) contacting the plastic material with at least one catalyst and at least one magnetic susceptor, wherein the at least one catalyst and the at least one magnetic susceptor are different from one another; and
(c) induction heating the plastic material, catalyst, and magnetic susceptor using a radio frequency (RF) field;
wherein the catalyst is doped with at least one metal or metalloid consisting of potassium, barium, lithium, sodium, rubidium, cesium, francium, beryllium, magnesium, calcium, strontium, radium, scandium, yttrium, lutetium, lawrencium, titanium, zirconium, hafnium, rutherfordium, zinc, cadmium, mercury, boron, aluminum, gallium, indium, thallium, germanium, tin, lead, platinum, palladium, nickel, or any combination thereof.

2. The method of claim 1, wherein the plastic material comprises low density polyethylene (LDPE), high density polyethylene (HDPE), polystyrene, polypropylene, polybutylenes, EPDM rubber, polyisoprene, styrene-butadiene rubber, poly(styrene-acrylonitrile) (SAN polymer), copolymers thereof, or any combination thereof.

3. The method of claim 1, wherein the plastic material comprises a virgin polymer, a recycled plastic, or any combination thereof.

4. The method of claim 3, wherein the recycled plastic comprises an LDPE grocery bag.

5. The method of claim 1, wherein the at least one catalyst comprises a crystalline aluminosilicate, aluminophosphate, or silicoaluminaphosphate catalyst, a cerium oxide-containing catalyst, or any combination thereof.

6. The method of claim 5, wherein the crystalline aluminosilicate, aluminophosphate, or silicoaluminaphosphate catalyst comprises Linde Type-L (LTL), ZSM-5 (MFI) or another member of the ZSM family, Beta (BEA), Theta-1 (TON), SSZ-13, or any combination thereof.

7. The method of claim 5, wherein the cerium oxide-containing catalyst comprises cerium oxide and zirconium oxide.

8. The method of claim 6, wherein the catalyst comprises Pt/K-MFI, PtSn/K-MFI, Pt/Ba-K-L, PtSn/K-L, Pt/K-TON, Pt/K-SSZ-13, or any combination thereof.

9. The method of claim 1, wherein the at least one magnetic susceptor comprises $Fe_3O_4$.

10. The method of claim 1, wherein the catalyst and magnetic susceptor are present in a weight ratio of from about 2:1 to about 1:2.

11. The method of claim 1, wherein a combined weight of the catalyst and magnetic susceptor and a weight of the plastic material are present in a ratio of from about 1:10 to about 1:2.

12. The method of claim 1, wherein the induction heating raises a temperature of the plastic material, catalyst, and magnetic susceptor to from about 200° C. to about 450° C., and wherein induction heating is carried out for from about 30 minutes to about 48 hours.

13. The method of claim 1, wherein the RF field has a current of from about 50 A to about 1000 A and a field strength of from about 10 mT to about 100 mT.

14. The method of claim 1, wherein the catalyst is resistant to coking, poisoning from plastic additives and residues, or both, and wherein the plastic additives and residues comprise antioxidants, flame retardants, plasticizers, food residue, green waste, or any combination thereof.

15. The method of claim 1, wherein the plastic material depolymerizes into $C_2$-$C_{20}$ alkanes or alkenes.

16. The method of claim 15, wherein the catalyst comprises PtSn/K-L or Pt/K-SSZ-13 and at least 90% of the plastic material depolymerizes into $C_2$-$C_{20}$ alkanes or alkenes.

17. The method of claim 15, wherein the catalyst comprises PtSn/K-L and wherein from about 30% to about 50% of the $C_2$-$C_{20}$ alkanes or alkenes are $C_6$-$C_{20}$ alkanes or alkenes.

18. The method of claim 15, wherein the catalyst comprises Pt/K-MFI and wherein from about 90% to about 99% of the $C_2$-$C_{20}$ alkanes or alkenes are $C_2$-$C_5$ alkanes or alkenes.

19. The method of claim 1, wherein the method produces less than 10 wt % coke on a carbon % basis.

* * * * *